US009186174B2

(12) United States Patent
Krishnan

(10) Patent No.: US 9,186,174 B2
(45) Date of Patent: Nov. 17, 2015

(54) METHODS AND SYSTEMS FOR ACCESSING A PERICARDIAL SPACE AND PREVENTING STROKES ARISING FROM THE LEFT ATRIAL APPENDAGE

(71) Applicant: Subramaniam Chitoor Krishnan, Sacramento, CA (US)

(72) Inventor: Subramaniam Chitoor Krishnan, Sacramento, CA (US)

(*) Notice: Subject to any disclaimer, the term of this patent is extended or adjusted under 35 U.S.C. 154(b) by 260 days.

(21) Appl. No.: 13/973,949

(22) Filed: Aug. 22, 2013

(65) Prior Publication Data
US 2014/0058371 A1 Feb. 27, 2014

Related U.S. Application Data

(60) Provisional application No. 61/692,171, filed on Aug. 22, 2012.

(51) Int. Cl.
*A61B 18/04* (2006.01)
*A61B 17/34* (2006.01)
*A61B 18/18* (2006.01)
(Continued)

(52) U.S. Cl.
CPC .......... *A61B 17/3417* (2013.01); *A61B 17/0057* (2013.01); *A61B 17/12013* (2013.01); *A61B 17/3478* (2013.01); *A61B 18/04* (2013.01); *A61B 18/1492* (2013.01); *A61B 18/18* (2013.01); *A61B 18/02* (2013.01); *A61B 18/082* (2013.01); *A61B 18/1477* (2013.01); *A61B 18/20* (2013.01); *A61B 2017/00247* (2013.01); *A61B 2017/00323* (2013.01); *A61B 2017/00876* (2013.01); *A61B 2017/0495* (2013.01); *A61B 2017/22069* (2013.01); *A61B 2018/0022* (2013.01); *A61B 2018/00285* (2013.01); *A61B 2018/00357* (2013.01);

(Continued)

(58) Field of Classification Search
CPC ........ A61B 18/02; A61B 18/04; A61B 18/08; A61B 18/082; A61B 18/10; A61B 18/12; A61B 18/1266; A61B 18/14; A61B 18/1477; A61B 18/1492; A61B 18/18; A61B 18/20; A61B 2018/0022; A61B 2018/00285; A61B 2018/00357; A61B 2018/00601; A61B 2018/046; A61B 17/0057; A61B 17/12013; A61B 17/3417; A61B 17/3478; A61B 2017/00247; A61B 2017/00323; A61B 2017/00876; A61B 2017/0495; A61B 2017/22069
USPC ................... 606/27, 33, 34, 41, 50; 604/96.01
See application file for complete search history.

(56) References Cited
U.S. PATENT DOCUMENTS 6,423,051 B1 7/2002 Kaplan et al.
7,951,069 B2 5/2011 Bertolero
(Continued)

*Primary Examiner* — Michael Peffley
*Assistant Examiner* — Khadijeh Vahdat
(74) *Attorney, Agent, or Firm* — Snell & Wilmer LLP

(57) ABSTRACT

The invention presents methods and systems for accessing a pericardial space and preventing strokes arising from a left atrial appendage ("LAA") by achieving a complete occlusion of the LAA using an epicardial approach without creating a puckering of the LAA ostium. A complete occlusion of the LAA is desired because bleeding arising from the LAA often leads to embolic strokes. Due to the peculiar anatomy of the LAA ostium, traditional LAA ligation techniques using sutures can lead to puckering, thus compromising the occlusion of the LAA. The invention achieves a complete occlusion and a more effective hemostatic seal with the use of inflatable balloons having electromagnetic coils internally, as well as hydrogels, sponges, and caliber tubes attached to the respective balloon's exterior, anchoring balloons, a closure device having a suture looped through two semi-rigid hollow tube that can be coated with hydrogel or silicone, and locking mechanisms.

11 Claims, 22 Drawing Sheets

(51) Int. Cl.
*A61B 17/00* (2006.01)
*A61B 17/12* (2006.01)
*A61B 18/02* (2006.01)
*A61B 18/08* (2006.01)
*A61B 18/14* (2006.01)
*A61B 18/20* (2006.01)
*A61B 18/00* (2006.01)
*A61B 19/00* (2006.01)
*A61N 7/02* (2006.01)
*A61B 17/04* (2006.01)
*A61B 17/22* (2006.01)

(52) U.S. Cl.
CPC  *A61B 2018/00601* (2013.01); *A61B 2018/046* (2013.01); *A61B 2019/5466* (2013.01); *A61N 7/022* (2013.01)

(56) References Cited

U.S. PATENT DOCUMENTS

| | | |
|---|---|---|
| 2004/0044361 A1 | 3/2004 | Frazier et al. |
| 2006/0027553 A1 | 2/2006 | Hanisko |
| 2007/0129753 A1 | 6/2007 | Quinn et al. |
| 2008/0183130 A1* | 7/2008 | Lutter ............... A61M 25/10 604/96.01 |
| 2009/0051270 A1 | 2/2009 | Yamazaki |
| 2010/0191279 A1 | 7/2010 | Kassab et al. |
| 2010/0286718 A1* | 11/2010 | Kassab ............ A61B 17/00491 606/158 |
| 2011/0082495 A1 | 4/2011 | Ruiz |
| 2011/0276075 A1 | 11/2011 | Fung et al. |
| 2012/0065667 A1 | 3/2012 | Javois et al. |

* cited by examiner

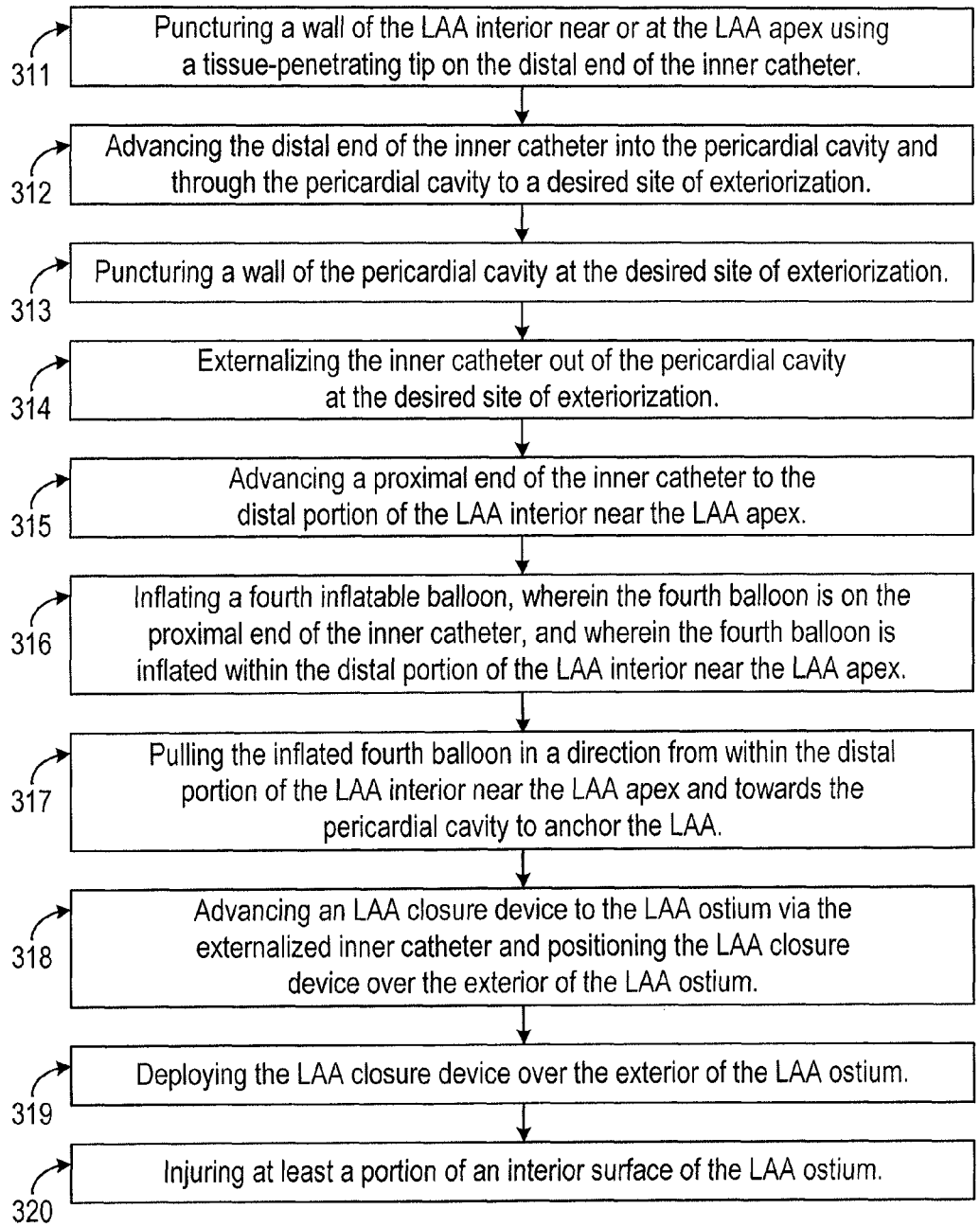
FIG. 3 (Con't)

METHODS AND SYSTEMS FOR ACCESSING A PERICARDIAL SPACE AND PREVENTING STROKES ARISING FROM THE LEFT ATRIAL APPENDAGE

CLAIM OF PRIORITY UNDER 35 U.S.C. §§119(e)-120

This application claims the benefit and priority under 35 U.S.C. §119(e) of U.S. Provisional Patent Application No. 61/692,171, entitled "METHODS AND SYSTEMS FOR ACCESSING A PERICARDIAL SPACE AND PREVENTING STROKES ARISING FROM THE HEART," filed on Aug. 22, 2012, the entire contents and disclosures of which are hereby incorporated by reference herein.

BACKGROUND

1. Field

The present invention relates to medical devices and medical methods. Specifically, the present invention relates to methods and systems for accessing a pericardial space and preventing strokes arising from a left atrial appendage ("LAA") by achieving a complete occlusion of the LAA using an epicardial approach without creating a puckering of the LAA ostium.

The LAA is a cylindrical, ear-shaped, and sometimes tortuous and pedunculated muscular pouch projecting from the upper anterior portion of the left atrium of the heart. The LAA is a long, tubular, hooked structure and has a narrow junction with the venous component of the atrium. Thus, the LAA lies within the pericardial space, and is an extension of the left atrium. The pericardial space is also commonly known as the pericardial cavity and thus, both terminologies are used synonymously herein. The LAA functions as a decompression chamber during left ventricular systole and during periods when left atrial pressure is high. The LAA is also commonly known as the left auricular appendix, the auricular, or the left auricle. The left atrium receives oxygenated blood from the lungs by way of the pulmonary veins, and pumps the oxygenated blood into the left ventricle via the mitral valve. The LAA is more distensible than the rest of the left atrium and for a given increase in pressure, expands more than the left atrium. In virtually all patients, the LAA has muscle bundles termed pectinate muscles that are more than 1-mm thick with deep crevices or recesses in-between. In addition, in the majority of hearts, distinct protrusions from the LAA body termed lobes are also present within the LAA. The LAA structure has received increasing attention over the past 15-20 years due to its propensity to be a site of blood clot formation especially in patients with atrial fibrillation ("AF"). AF is the most common cause of strokes arising from the heart.

AF patients have a five-fold increased risk of an embolic stroke resulting primarily from thromboembolic events. There is very strong evidence that strokes which occur in AF are thromboembolic, such as, a blood clot which formed in the heart and then breaks off and travels to the blood vessel in the brain. In non-rheumatic AF patients, the stroke-causing thrombus originates almost exclusively from the LAA. Typically, the thrombus formed in the LAA break away from the LAA and accumulates in other blood vessels, thereby blocking blood flow in these blood vessels, and ultimately leading to an embolic stroke. Cardio-embolic strokes related to AF are large and prone to early recurrence with higher mortality. An antithrombotic or anticoagulant drug is one that suppresses, delays, or nullifies blood coagulation. Treatment with antithrombotic agents, such as warfarin, has been the "cornerstone" of medical therapy for these AF patients, but it can be difficult to maintain dosage within the therapeutic range and administration requires frequent monitoring and dose adjustments. Moreover, anticoagulants are associated with undesirable side effects, many of which are exacerbated with advanced age. As high as 50% of elderly patients are not offered anti-coagulation therapy even though they are at the greatest risk of development of embolic strokes. Therefore, alternative management strategies have been proposed, especially for the elderly, depending on the severity of the condition.

As such, the source of the blood clot must be identified to prevent recurrences and thus provide effective alternative therapy. It has been established that AF-related emboli originate primarily in the LAA. Based on this knowledge, procedures have been developed where the LAA is obliterated or excised and thus excluded from the systemic circulation. The aim is to prevent or inhibit thrombi in the LAA from embolizing into the systemic circulation. These procedures include (a) surgeries where the LAA is stapled with an amputating stapling device or sutured closed and/or excised and (b) endocardial procedures where an occlusive device is placed inside the LAA. Both approaches have been successful and are being tested, but also have very significant limitations.

Using stapling and similar technologies to exclude the LAA is often associated with incomplete closure leaving behind a stump. This stump can often serve as a source of future embolism. Similarly endocardial devices also have their share of problems. First, accurate placement of an endocardial device is highly dependent on the anatomy of the LAA, which is unpredictable because the shape and size of the LAA can vary widely. Other limitations of endocardial devices include the use of fixation barbs which can traumatize the LAA wall and incomplete occlusion due to gaps between the endocardial device and the LAA wall. There is also the possibility that the endocardial device may be by itself thrombogenic and it is constantly in contact with left atrial blood. A clip or a suture that is placed outside the heart does not come into contact with blood in the LAA cavity, and is less impacted by the LAA anatomy. The novel technology presented in this invention allows a puncture from the LAA onto the pericardial space in a controlled setting without the development of hemorrhage into the pericardial space. Following this, a catheter is exteriorized and over this, a closure device is inserted via the pericardial space that then clamps shut the LAA ostium.

2. Description of the Related Art

A number of approaches for plugging the LAA with an implantable device delivered via an endovascular approach have been proposed. In particular, occlusion of the LAA is believed to decrease the risk of an embolic stroke in non-valvular AF patients. By occluding the LAA, the thrombus formed in the LAA are unable to migrate to other blood vessels, thereby reducing the risks of thromboembolism and embolic stroke. Hence, the occlusion of the LAA is believed to be an effective stroke prevention strategy in non-valvular AF patients. Indeed, this concept of occluding the LAA as a stroke prevention strategy is being increasingly tested with implantable medical devices that occlude the LAA using an endocardial and epicardial approaches.

An example of an endocardial approach is the WATCHMAN device developed by Atritech Inc. (located in Plymouth, Minn.). The WATCHMAN device is an implantable device designed to occlude the LAA in non-valvular AF patients. The WATCHMAN device is delivered to the LAA via an endovascular approach and is placed distal to the LAA ostium, which upon expansion, occludes the LAA. The occlusion of the LAA prevents the migration of the thrombus formed in the LAA, thereby reducing the risks of thromboembolism and embolic stroke. In the WATCHMAN device's clinical trial, PROTECT-AF, the results showed that in AF patients who were candidates for warfarin therapy, the closure of the LAA using the WATCHMAN device was associated with a reduction in hemorrhagic stroke risk as compared to warfarin therapy. Additionally, these results showed that all-cause stroke and all-cause mortality outcomes were non-inferior to warfarin.

However, the WATCHMAN device's "one size or one shape fits all" approach results in several limitations, such as inadequate circulatory exclusion of the LAA. For example, a major limitation of the WATCHMAN device is the incomplete occlusion of the LAA because it is relatively common for there to be a gap between the WATCHMAN device surface and the LAA wall. These gaps are more likely to enlarge over time and persist, while new gaps also occur during follow up. Gaps are also commonly noted to enlarge over time, and new gaps occur during follow up even if the LAA was completely sealed at implantation. The long, tortuous and pedunculated structure of the LAA can make it difficult to seat the device within the LAA cavity. This can result in the device placed in a suboptimal manner with incomplete occlusion, and an incomplete occlusion is worse than no occlusion. The present invention provides for more refined systems and methods for achieving a complete occlusion of the LAA.

Another limitation of the WATCHMAN device is the fixation of barbs or wires engaged in the walls of the LAA. As shown in the WATCHMAN device's PROTECT-AF trial, major adverse events include bleeding and pericardial effusion. Pericardial effusion is the abnormal accumulation of fluid in the pericardial cavity, which can negatively affect heart function. The present invention provides for more refined systems and methods for achieving a complete occlusion of the LAA without the risks associated with tears or bleeding arising from the fixation of barbs or wires engaged in the LAA walls and without implanted hardware that is constantly exposed to blood in the LAA cavity.

More recently, EpiTek Inc. (located in Bloomington, Minn.) and SentreHEART, Inc. (located in Redwood City, Calif.) have each developed implantable devices designed to occlude the LAA. The SentreHEART, Inc.'s device is called the LARIAT. These devices are introduced percutaneously into the pericardial cavity, also known as the pericardial space, and then used to place a suture circumferentially at the ostium of the LAA, typically referred to as LAA ligation. Pericardial access is typically established via a subxiphoid approach with a needle. A wire is placed through the needle into the pericardial cavity. A sheath is then placed in the pericardial space through which a catheter is advanced to the desired location. The procedure of obtaining pericardial access with a needle via a subxiphoid approach can be technically difficult, and associated complications include lacerations of the myocardium, the coronary arteries and veins. Unlike the Epitek device, the LARIAT device also involves placement of a balloon within the LAA. Using magnetic forces, the wire within the pericardial space and the balloon in the LAA are made to come into contact. A pre-tied suture that is placed around the LAA is advanced from the exterior over the wire and balloon and then tightened. Due to the severe technical limitations associated with the procedure, it has not been adopted in a widespread manner. The present invention provides for an anchoring hemostatic mechanism that makes the procedure of accessing the pericardial space safer and less difficult.

LAA ligation from a circumferentially applied suture or tie also suffers from puckering of the occlusion which can compromise sealing. In addition to causing a puckering and incomplete occlusion of the LAA ostium, a circumferential suture also has the disadvantage of having a potential to cause a tear or laceration of the LAA. It is anticipated that in the elderly hearts (the elderly patients are the primary candidates of this approach), which are known to be delicate, this approach may be associated with an even greater risk of bleeding and tears. In the event of a tear of the LAA in the elderly hearts, there is a high likelihood of this being fatal. This is an emergent situation and there will not be time to transfer the patient to the operating room. The present invention provides for more refined systems and methods for achieving a complete occlusion of the LAA without creating a puckering effect.

For the foregoing reasons, there is a need for novel technology to achieve a complete occlusion of the LAA without creating a puckering of the LAA ostium. The present invention addresses this need by presenting methods and systems for achieving a complete occlusion of the LAA using an epicardial approach without creating a puckering of the LAA ostium.

Additionally, within the last decade, there has been an increasing use of a surgically deployable metallic clip that can be place around the base of the LAA. The most prominent among these is the AtriClip manufactured by AtriCure Inc. (located in Cincinnati, Ohio) described in U.S. Patent Application Nos. 2006/027553 and 2009/051270. The AtriClip is made of two parallel rigid titanium tubes with elastic nitinol springs covered with a knit-braided polyester sheath. Deploying the AtriClip is a surgical procedure that requires the chest in between the ribs to be cut open rather than a puncture and is placed over the LAA under direct visualization. It is not a minimally invasive procedure that is necessarily performed by the surgeon rather than the cardiologist.

Methods and apparatus for accessing a pericardial space and optionally placing an external closure over the LAA are described in U.S. Pat. No. 6,423,051; U.S. Pat. No. 7,951,069; and U.S. Patent Application No. 2011/276,075 ("the '075 Application").

The present invention is distinguished from the aforementioned references for at least the following reasons. In particular, the '075 Application only discloses a single occlusion member to occlude the LAA that is then followed by an intentional perforation of the LAA to obtain access to the pericardial space. The catheter is then exteriorized and using the exteriorized catheter as a railing, a suture is delivered to ligate the LAA. Moreover, the '075 Application only discloses an occlusion member inflated within the LAA, in which this one inflated balloon is used to occlude the entirety of the LAA cavity. By contrast, the focus of the current invention is to limit or eliminate blood flow through the neck-like ostium of the LAA. This is achieved by the expansion of a plurality of inflatable balloons immediately across the LAA ostium both within the LAA and in the left atrial cavity. The LAA wall has thick muscle bundles that are more than 1-mm thick with deep recesses in-between the bundles, giving it a rough appearance. Protrusions from the LAA wall termed lobes are also seen in the majority of the hearts. Due to these recesses and lobes, a single occlusion member within the LAA cavity is unlikely to provide an effective hemostatic seal. By contrast, the present invention presents a plurality of inflatable balloons to provide an effective hemostatic seal.

In the present invention, the main occluding element is deployed within the cavity of the left atrium, rather than within the LAA. This main occluding element, such as an inflatable balloon, has dimensions larger than the LAA ostium when inflated. Thus, when inflated, this main occluding element envelops the LAA ostium. This main occluding element's surface is in contact with the smooth surface of the left atrial cavity wall and upon full deployment, is able to provide an effective hemostatic seal.

The primary purpose of the expandable elements that are within the LAA, rather than to achieve a hemostatic seal, is to pull the left atrium cavity balloon towards the LAA ostium (by application of electromagnetic forces) and to jam it shut. In an exemplary embodiment, the present invention has the presence of thin tubes attached to the balloon surface of the left atrium cavity balloon. These tubes allow for the application of vacuum or suction forces that will be applied against the smooth-walled left atrium to allow for a more effective hemostatic seal.

The use of multiple inflatable balloons to create a tight hemostatic seal for occluding the LAA ostium is not presented in the prior art. In particular, at least one of the inflatable balloons occluding the LAA ostium is non-compliant, such that upon inflation of the non-compliant balloon, the surrounding LAA walls are expanded to accentuate the constriction that one would expect at the LAA ostium. The use of these multiple inflatable balloons distinguishes the present invention from the prior art's single occlusion element that is placed within the LAA cavity. Hence, the present invention should not result in gaps between the occlusion element's surface and the LAA walls. Second, the use of electromagnetic coils within the inflatable balloons, wherein upon inflation of these balloons, the electromagnetic coils also expand within these balloons, is not present in the prior art. These electromagnetic coils further enhance the hemostatic seal by way of electromagnetic forces between the inflated balloons occluding the LAA ostium. The use of the electromagnetic coils ensures that the present invention does not result in gaps between the occlusion element's surface and the LAA walls.

Another novel feature of the present invention is the coating of the inflatable balloons with biocompatible hydrogels to provide a superior seal. Also novel is the presence of tubules attached primarily to the left atrial cavity balloon will allow for the vacuum or suction forces that are applied from an external source. This will result in the left atrial and LAA tissues adhering to the balloons more effectively, thus resulting in a superior seal.

The present invention's closure device comprising of a suture looped around two semi-rigid tubes further distinguishes the present invention from the prior art. The present invention's closure device ensures that there shall be no puckering effect around the LAA ostium commonly seen in the prior art, such as with the devices developed by EpiTek Inc. and SentreHEART, Inc. Additionally, the coating of hydrogel or silicone to the interior surfaces of the two semi-rigid tubes is another novel feature, ensuring that there is no puckering effect. Moreover, an anchoring balloon attached to the exteriorized catheter used to stabilize the LAA while the closure device is being deployed to the LAA ostium is yet another distinguishing novel feature. This anchoring mechanism ensures that the exteriorized catheter, when pulled externally is able to have its proximal end within the LAA cavity, after the hemostatic balloons have been deflated and removed. Furthermore, the present invention provides for an injuring step that is not present in the prior art. Specifically, the injury step is designed to induce to induce a tissue response that enhances the closure and sealing of the LAA ostium.

The present invention can also be used for other purposes to canulate the pericardial cavity. In case it is decided to not occlude the LAA ostium at the end of the procedure, the site of puncture in LAA can be sutured closed with an absorbable or non-absorbable suture (with or without a collagen pledget) applied from the exterior.

It is also anticipated that the present invention can be used to occlude or ligate any tubular structure (vascular or otherwise) within the body (for example an aneurysm).

UNDERLYING PRINCIPLES OF THE PRESENT INVENTION

Unlike the right atrial appendage which has a broad based pyramidal shape, the cylindrical pedunculated shape of the LAA and the presence of a narrow waist or constriction at the LAA ostium allows this structure to be occluded by the placement of expanding elements within or adjacent to the LAA. The LAA is also more compliant compared to the left atrial cavity allowing for balloons to be inflated within the LAA.

Occluding the LAA allows for the controlled puncture of the LAA where access to the pericardium can be obtained from the left atrial cavity, without any bleeding occurring into the pericardial space. The catheter that is placed in the pericardium can now puncture the parietal pericardium and be exteriorized for example in the subxiphoid region. This can be used to deliver materials and devices to the pericardial space in a safe manner.

However, inflating a cylindrical balloon within the LAA is unlikely to provide a safe and stable hemostatic occlusive seal for the following reasons. The first reason is the presence of pectinate muscles and lobes in the LAA. Nearly all adult LAAs contain pectinate muscles that are greater than 1-mm in diameter. As a result of these pectinate muscles, the LAA has a rough quality unlike the left atrial cavity, which is smooth-walled. Deep recesses are present in the LAA in-between these pectinate muscles. The LAA also has the presence of larger distinct protrusions termed lobes. The presence of these lobes and recesses makes it difficult for a single balloon inflated within the LAA to provide an effective seal since the cavity of the lobes and the recesses would allow for blood through flow through.

In some hearts, a distinct constriction is absent at the ostium of the LAA. In some atria, the constriction when present at the LAA ostium is not circumferential. This raises the possibility that upon inflation of a single balloon within the LAA, this inflated balloon may fall out of the LAA into the left atrial cavity.

The novel invention presented in this application solves the above mentioned problems through the following innovations illustrated by the hour-glass concept.

The Hour-Glass Concept.

The Hour-Glass concept presents the importance of multiple inflatable balloons in controlling the neck of the hour-glass. One of the key factors affecting the time measured in the hour-glass is the neck width. The neck of the hour-glass represents the LAA ostium. The top bulb of the hour-glass represents the left atrial cavity while the bottom bulb of the house-glass represents the LAA. This hour-glass concept as it relates to the LAA was conceived by the named inventor on this patent application.

The current invention is based on the concept that preventing the sand or water flowing from the top bulb to the bottom, which is achieved by occluding or sandwiching the neck by a combination of inflatable balloons that are deployed across the constriction and forced towards each other rather by inflating a single balloon in the bottom bulb only. These inflatable balloons that are placed immediately across the neck are approximated towards each other by a combination of pushing and pulling, as detailed in FIGS. 17-18. A first balloon is inflated within the LAA adjacent to the LAA ostium and a second balloon is inflated within the distal portions of the LAA. The inflated second balloon pushes the inflated first balloon towards the neck of the hour-glass, which represents the LAA ostium. The inflated first balloon is also pulled towards the neck of the hour-glass by manual traction on the inner sheath.

A third balloon is inflated within the left atrial cavity adjacent to the LAA ostium. Electromagnetic coils can also be present within the first and the third balloon. The electromagnetic coils in the inflated third balloon also pull the inflated first balloon towards the neck of the hour-glass by way of electromagnetic forces. Conversely, the electromagnetic coils in the inflated first balloon pull the inflated third balloon towards the neck of the hour-glass by way of electromagnetic forces. Thus, the main function of the inflated first balloon is to pull the inflated third balloon towards the LAA ostium by way of electromagnetic forces. The main function of the inflated second balloon is the push the inflated first balloon towards the LAA ostium.

The present invention presents the accentuation or exaggeration of the LAA ostium by inflating a non-compliant balloon within the LAA adjacent to the LAA ostium. The first inflatable balloon is non-compliant and inflated with higher pressure. A non-compliant balloon is likely to deform the LAA walls and by creating expanding the LAA walls, it will accentuate the neck of the hour-glass and allow for a better approximation of the inflated balloons against the surfaces. (Hoit B D, Walsh R: Regional atrial distensibility. American Journal of Physiology 1992; 262:H1356-H1360). The LAA is more distensible than the left atrial cavity and hence should readily deform especially in response to high pressure inflation with a non-compliant balloon. The inflated non-compliant first balloon is then forced towards the LAA ostium by a combination of pushing and pulling.

The second balloon is largely compliant and is inflated within the distal portion of the LAA. Upon inflation, the second balloon conforms to the LAA anatomy and pushes the inflated first balloon further towards the LAA ostium, as shown on FIGS. 17-18. Additionally, the inflated second balloon prevents the inflated first balloon from being pushed away from the LAA ostium.

The third balloon, which is located on the outer sheath, is inflated within the left atrial cavity adjacent to the LAA ostium and is pushed towards the LAA ostium. Thus, the inflated third balloon envelops the LAA ostium. The inflated first and third balloons are manually pushed towards each other by pulling on the inner sheath and pushing on the outer sheath.

The present invention guards against the possibility of the inflated first balloon falling out of the LAA and into the left atrial cavity. In particular, the inflated third balloon has an additional function of preventing the inflated first balloon from falling into the left atrial cavity especially in the setting of an indistinct LAA ostium where a constriction is absent. Additionally, a locking mechanism is described where the inner and outer sheaths lock on to each other. This locking mechanism may be present intravascular, intracardiac, or outside the body. In addition, an additional inflatable balloon that is attached to the outer sheath can be inflated immediately to the left of the interatrial septum to render the outer sheath stationary.

The LAA ostium has an oval shape. Applying a circumferential tie or suture to the LAA ostium is going to compress a fixed circumference to a smaller area and therefore will cause puckering. Puckering is more likely to cause gaps and incomplete occlusion. A suture is also more likely to cause tears in the LAA especially in elderly hearts. A closure device that approximates the opposing surfaces is a better approach and is unlikely to cause puckering. The present invention presents a novel closure device that approximates surfaces opposite to each other and brings them into contact is a better approach. This is most effectively created by applying forces along the short axis or short diameter of the oval or elliptical ostium. Hence, a barrette or clip applied at the ostium of the LAA is more likely to seal off the structure. Force applied along the long diameter is less likely to approximate the opposite surfaces since (a) the two surfaces will have to travel a longer distance and (b) a greater amount of force will be necessary to overcome the intrinsic tissue elasticity.

Creating endothelial denudation at the LAA ostium by intentional injury will create inflammation and cross-linking of collagen fibers, resulting in more durable occlusion of the LAA ostium. The present invention provides such a feature. For example, endothelial denudation at the LAA ostium can be created by application radiofrequency (RF) current via the inflatable balloons at the LAA ostium.

SUMMARY OF THE INVENTION

The present invention addresses the foregoing needs with novel methods and systems for accessing a pericardial space and preventing strokes arising from the LAA by achieving a complete occlusion of the LAA using an epicardial approach without creating a puckering of the LAA ostium. The contents of this summary section are provided only as a simplified introduction to the invention, and are not intended to be used to limit the scope of the appended claims.

In an exemplary embodiment, the present invention's system comprises a catheter having an inner sheath, an outer sheath, and an inner catheter; the inner sheath having a distal end and a proximal end, wherein the distal end has at least two inflatable balloons; the outer sheath having a distal end and a proximal end, wherein the distal end has at least one inflatable balloon; the inner catheter having a distal end and a proximal end, wherein the distal end has a tissue-penetrating tip, and wherein the proximal end has at least one inflatable balloon serving as an anchor; locking means to lock the inner sheath and the outer sheath; an inflation port; a control port; and a closure device having a suture looped around at least two semi-rigid hollow tubes.

In another exemplary embodiment, the present invention's system comprises a catheter having an inner sheath, an outer sheath, and an inner catheter; the inner sheath having a distal end and a proximal end, wherein the distal end has at least two inflatable balloons; the outer sheath having a distal end and a proximal end, wherein the distal end has at least one inflatable balloon; the inner catheter having a distal end and a proximal end, wherein the distal end has a tissue-penetrating tip, wherein the tissue-penetrating tip is a sharpened tip capable of puncturing (a) a wall of the LAA, and (b) a wall of a pericardial cavity, and wherein the proximal end has at least one inflatable balloon serving as an anchor; locking means to lock the inner sheath and the outer sheath; an inflation port; a control port; and a closure device having a suture looped around at least two semi-rigid hollow tubes.

In another exemplary embodiment, the present invention's system comprises a catheter having an inner sheath, an outer sheath, and an inner catheter; the inner sheath having a distal end and a proximal end, wherein the distal end has at least two inflatable balloons; the outer sheath having a distal end and a proximal end, wherein the distal end has at least one inflatable balloon; the inner catheter having a distal end and a proximal end, wherein the distal end has a tissue-penetrating tip, wherein the tissue-penetrating tip is a sharpened tip capable of puncturing (a) a wall of the LAA, and (b) a wall of a pericardial cavity, wherein the tissue-penetrating tip further has a RF electrode delivering RF current that can puncture (a) a wall of the LAA, and (b) a wall of a pericardial cavity, and wherein the proximal end has at least one inflatable balloon serving as an anchor; locking means to lock the inner sheath and the outer sheath; an inflation port; a control port; and a closure device having a suture looped around at least two semi-rigid hollow tubes.

In another exemplary embodiment, the present invention's system comprises a catheter having an inner sheath, an outer sheath, and an inner catheter; the inner sheath having a distal end and a proximal end, wherein the distal end has at least two inflatable balloons, wherein at least one inflatable balloon of the inner sheath has a first set of electromagnetic coils, wherein the first set of electromagnetic coils expands within the balloon upon inflation of the balloon, and wherein at least one inflatable balloon of the outer sheath has a second set of electromagnetic coils, wherein the second set of electromagnetic coils expands within the balloon upon inflation of the balloon; the outer sheath having a distal end and a proximal end, wherein the distal end has at least one inflatable balloon; the inner catheter having a distal end and a proximal end, wherein the distal end has a tissue-penetrating tip, and wherein the proximal end has at least one inflatable balloon serving as an anchor; locking means to lock the inner sheath and the outer sheath; an inflation port; a control port; and a closure device having a suture looped around at least two semi-rigid hollow tubes.

In another exemplary embodiment of the inventive system, the present invention's system comprises a catheter having an inner sheath, an outer sheath, and an inner catheter; the inner sheath having a distal end and a proximal end, wherein the distal end has at least two inflatable balloons; the outer sheath having a distal end and a proximal end, wherein the distal end has at least one inflatable balloon; the inner catheter having a distal end and a proximal end, wherein the distal end has a tissue-penetrating tip, and wherein the proximal end has at least one inflatable balloon serving as an anchor; locking means to lock the inner sheath and the outer sheath; an inflation port; a control port; and a closure device having a suture looped around at least two semi-rigid hollow tubes, and wherein the closure device further comprises hydrogel coated over at least an inner surface of the pair of semi-rigid hollow tubes.

In another exemplary embodiment of the inventive system, the present invention's system comprises a catheter having an inner sheath, an outer sheath, and an inner catheter; the inner sheath having a distal end and a proximal end, wherein the distal end has at least two inflatable balloons; the outer sheath having a distal end and a proximal end, wherein the distal end has at least one inflatable balloon; the inner catheter having a distal end and a proximal end, wherein the distal end has a tissue-penetrating tip, and wherein the proximal end has at least one inflatable balloon serving as an anchor; locking means to lock the inner sheath and the outer sheath; an inflation port; a control port; and a closure device having a suture looped around at least two semi-rigid hollow tubes, and wherein the closure device further comprises silicone gel coated over at least an inner surface of the pair of semi-rigid hollow tubes.

In another exemplary embodiment, the present invention's system comprises a catheter having an inner sheath, an outer sheath, and an inner catheter; the inner sheath having a distal end and a proximal end, wherein the distal end has at least two inflatable balloons; the outer sheath having a distal end and a proximal end, wherein the distal end has at least two inflatable balloons, wherein at least one balloon serves as an anchor; the inner catheter having a distal end and a proximal end, wherein the distal end has a tissue-penetrating tip, and wherein the proximal end has at least one inflatable balloon serving as an anchor; locking means to lock the inner sheath and the outer sheath; an inflation port; a control port; and a closure device having a suture looped around at least two semi-rigid hollow tubes.

In another exemplary embodiment, the present invention's system comprises a catheter having an inner sheath, an outer sheath, and an inner catheter; the inner sheath having a distal end and a proximal end, wherein the distal end has at least two inflatable balloons that are coated with biocompatible hydrogel; the outer sheath having a distal end and a proximal end, wherein the distal end has at least one inflatable balloon, wherein at least one balloon serves as an anchor; the inner catheter having a distal end and a proximal end, wherein the distal end has a tissue-penetrating tip, and wherein the proximal end has at least one inflatable balloon serving as an anchor; locking means to lock the inner sheath and the outer sheath; an inflation port; a control port; and a closure device having a suture looped around at least two semi-rigid hollow tubes.

In another exemplary embodiment, the present invention's system comprises a catheter having an inner sheath, an outer sheath, and an inner catheter; the inner sheath having a distal end and a proximal end, wherein the distal end has at least two inflatable balloons having sponges attached to the exterior of each balloon; the outer sheath having a distal end and a proximal end, wherein the distal end has at least one inflatable balloon, wherein at least one balloon serves as an anchor; the inner catheter having a distal end and a proximal end, wherein the distal end has a tissue-penetrating tip, and wherein the proximal end has at least one inflatable balloon serving as an anchor; locking means to lock the inner sheath and the outer sheath; an inflation port; a control port; and a closure device having a suture looped around at least two semi-rigid hollow tubes.

In another exemplary embodiment, the present invention's system comprises a catheter having an inner sheath, an outer sheath, and an inner catheter; the inner sheath having a distal end and a proximal end, wherein the distal end has at least two inflatable balloons; the outer sheath having a distal end and a proximal end, wherein the distal end has at least one inflatable balloon having caliber tubes attached to the exterior of the balloon, wherein at least one balloon serves as an anchor; the inner catheter having a distal end and a proximal end, wherein the distal end has a tissue-penetrating tip, and wherein the proximal end has at least one inflatable balloon serving as an anchor; locking means to lock the inner sheath and the outer sheath; an inflation port; a control port; and a closure device having a suture looped around at least two semi-rigid hollow tubes.

In another exemplary embodiment, the present invention's system comprises a catheter having an inner sheath, an outer sheath, and an inner catheter; the inner sheath having a distal end and a proximal end, wherein the distal end has at least two inflatable balloons; the outer sheath having a distal end and a proximal end, wherein the distal end has at least two inflatable balloons, wherein at least one balloon serves as an anchor, and at least one balloon has caliber tubes attached to the exterior of the balloon; the inner catheter having a distal end and a proximal end, wherein the distal end has a tissue-penetrating tip, and wherein the proximal end has at least one inflatable balloon serving as an anchor; locking means to lock the inner sheath and the outer sheath; an inflation port; a control port; and a closure device having a suture looped around at least two semi-rigid hollow tubes.

In another exemplary embodiment, the present invention's system comprises a catheter having an inner sheath, an outer sheath, and an inner catheter; the inner sheath having a distal end and a proximal end, wherein the distal end has at least two inflatable balloons and at least one radiopaque marker band; the outer sheath having a distal end and a proximal end, wherein the distal end has at least one inflatable balloon; the inner catheter having a distal end and a proximal end, wherein the distal end has a tissue-penetrating tip, wherein the tissue-penetrating tip, and wherein the proximal end has at least one inflatable balloon serving as an anchor; locking means to lock the inner sheath and the outer sheath; an inflation port; a control port; and a closure device having a suture looped around at least two semi-rigid hollow tubes.

In an exemplary embodiment, the present invention's method comprises the steps of (1) introducing catheter into a body cavity, the catheter having an inner sheath, an outer sheath, and an inner catheter; (2) advancing a distal end of the inner sheath to position the distal end of the inner sheath in an interior of an LAA; (3) inflating a first inflatable balloon, wherein the first balloon is on the distal end of the inner sheath, and wherein the first balloon is inflated within the LAA interior adjacent to an ostium of the LAA; (4) pulling the inflated first balloon in a direction from within the LAA interior and towards the LAA ostium; (5) inflating a second inflatable balloon, wherein the second balloon is on the distal end of the inner sheath, wherein the second balloon is inflated within a distal portion of the LAA interior, and wherein upon inflation, the inflated second balloon pushes the inflated first balloon towards the LAA ostium; (6) advancing a distal end of the outer sheath to position the distal end of the outer sheath in a portion of the left atrium adjacent to the LAA ostium; (7) inflating a third inflatable balloon, wherein the third balloon is on the distal end of the outer sheath, and wherein the third balloon is inflated within a portion of the left atrium adjacent to the LAA ostium; (8) pushing the inflated third balloon in a direction from within the left atrium portion adjacent to the LAA ostium and towards the LAA ostium; (9) activating a locking mechanism to lock the inner sheath to the outer sheath, thereby rendering stationary the inflated balloons; (10) advancing a distal end of the inner catheter to position a distal end of the inner catheter within a distal portion of the LAA interior near an apex of the LAA; (11) puncturing a wall of the LAA interior near or at the LAA apex using a tissue-penetrating tip on the distal end of the inner catheter; (12) advancing the distal end of the inner catheter into the pericardial cavity and through the pericardial cavity to the desired site of exteriorization; (13) puncturing a wall of the pericardial cavity at the desired site of exteriorization; (14) externalizing the inner catheter out of the pericardial cavity at the desired site of exteriorization, wherein the inner catheter can be externalized or "pushed out" with a combination of manual force, electromagnetic force, and/or radio frequency energy delivery; (15) advancing a proximal end of the inner catheter to the distal portion of the LAA interior near the LAA apex; (16) inflating a fourth inflatable balloon, wherein the fourth balloon is on the proximal end of the inner catheter, and wherein the fourth balloon is inflated within the distal portion of the LAA interior near the LAA apex; (17) pulling the inflated fourth balloon in a direction from within the distal portion of the LAA interior near the LAA apex and towards the pericardial cavity to anchor the LAA; (18) advancing an LAA closure device to the LAA ostium via the externalized inner catheter and positioning the LAA closure device over the exterior of the LAA ostium; (19) deploying the LAA closure device over the exterior of the LAA ostium; and (20) injuring at least a portion of an interior surface of the LAA ostium to promote occlusion of the LAA.

In another exemplary embodiment, the present invention's method further comprises the following features. For brevity, steps (1)-(20) of the exemplary embodiment of the present invention's method are incorporated herein. At steps (3) and (7), the first and third inflatable balloons each have a set of electromagnetic coils located within. Upon inflation of these balloons, the respective sets of electromagnetic coils also expand within the respective balloon. The expansion of the electromagnetic coils creates electromagnetic forces that attract the first and third inflated balloons towards each other.

In another exemplary embodiment, the present invention's method further comprises the following features. For brevity, steps (1)-(20) of the exemplary embodiment of the present invention's method are incorporated herein. At steps (3) and (5), the first and second inflatable balloons have biocompatible hydrogel coated to the exterior of each balloon. Upon inflation of these balloons, the biocompatible hydrogel expands on contact with fluid, such as blood.

In another exemplary embodiment, the present invention's method further comprises the following features. For brevity, steps (1)-(20) of the exemplary embodiment of the present invention's method are incorporated herein. At step (7), the third inflatable balloon has caliber tubes attached to its exterior. These tubes will allow for the application of vacuum or suction forces to the left atrial tissue to provide for a tighter hemostatic seal.

In another exemplary embodiment, the present invention's method further comprises the following features. For brevity, steps (1)-(20) of the exemplary embodiment of the present invention's method are incorporated herein. At steps (11) and (13), the tissue-penetrating tip is a sharpened tip capable of puncturing (a) the wall of the LAA, and (b) the wall of the pericardial cavity. The penetrating tip may further comprise a RF electrode delivering RF current sufficient to puncture (a) the wall of the LAA, and (b) the wall of the pericardial cavity.

In another exemplary embodiment, the present invention's method further comprises the following features. For brevity, steps (1)-(20) of the exemplary embodiment of the present invention's method are incorporated herein. At steps (12) to (14), the desired site of exteriorization is at the junction of the abdomen and thorax and below the ribs near a base of the sternum called a xiphisterum so that the inner catheter follows a subxiphoid path.

In another exemplary embodiment, the present invention's method further comprises the following features. For brevity, steps (1)-(20) of the exemplary embodiment of the present invention's method are incorporated herein. At steps (12) to (14), the desired site of exteriorization is at the junction of the abdomen and thorax and below the ribs near a base of the sternum called a xiphisterum so that the inner catheter follows a subxiphoid path. In other exemplary embodiments, the desired sites of exteriorization include the right pectoral regions, the left pectoral regions, or any other region higher up in the chest, lateral to the sternum between the ribs.

In another exemplary embodiment, the present invention's method further comprises the following features. For brevity, steps (1)-(20) of the exemplary embodiment of the present invention's method are incorporated herein. At step (14), the inner catheter can be "pulled out" from the pericardial cavity with electromagnetic forces applied with another catheter having an electromagnetic probe that is placed at the desired site of exteriorization. A small incision can be made in the skin to the left of the xiphisternum, or higher up in the chest, for example, lateral to the sternum between the ribs. An electromagnetic probe is introduced towards the pericardial cavity through this incision to attract the inner catheter (that has electromagnets incorporated) that is then exteriorized. The distal end of the inner catheter would comprise an electromagnetic element, which interacts with the electromagnetic probe adapted to draw the inner catheter out of the pericardial cavity.

In another exemplary embodiment, the present invention's method further comprises the following features. For brevity, steps (1)-(20) of the exemplary embodiment of the present invention's method are incorporated herein. At step (19), the closure device may be coated over at least an inner surface with a hydrogel, silicone gel, and/or other biocompatible material. Hydrogels will expand on contact with fluid, such water or blood, to further compress the LAA ostium.

In another exemplary embodiment, the present invention's method further comprises the following features. For brevity, steps (1)-(20) of the exemplary embodiment of the present invention's method are incorporated herein. Between steps (08) and (09) is an additional step, wherein this step includes inflating an additional balloon within a portion of the left atrium adjacent to the interatrial septum to render stationary the outer sheath. This additional balloon is on the distal end of the inner sheath and serves to anchor in-place the outer sheath and the other inflated balloons. Alternatively, this additional balloon can inflated adjacent the *fossa ovalis*. Optionally, a locking mechanism can be activated to render stationary the outer sheath and this inflated additional balloon adjacent to the interatrial septum. This locking mechanism can be deployed after the inflation of this additional balloon but before step (09). The locking mechanism would be similar to the one deployed in step (09).

In another exemplary embodiment, the present invention's method further comprises the following features. For brevity, steps (1)-(20) of the exemplary embodiment of the present invention's method are incorporated herein. After step (20), this alternate exemplary embodiment further includes the steps of: deflating the first inflated balloon, deflating the second inflated balloon, deflating the third inflated balloon, deactivating the locking mechanism, removing the outer sheath from the body cavity, and removing the inner sheath from the body cavity.

BRIEF DESCRIPTION OF THE DRAWINGS

Other systems, methods, features and advantages of the present invention will be, or will become, apparent to one of ordinary skill in the art upon examination of the following figures and detailed description. It is intended that all such additional apparatuses, systems, methods, features and advantages be included within this description, be within the scope of the present invention, and be protected by the appended claims. Component parts shown in the drawings are not necessarily to scale, and may be exaggerated to better illustrate the important features of the present invention. In the drawings, like reference numerals designate like parts throughout the different views, wherein:

FIG. 6 illustrates the advancement of the inner catheter through the wall of the LAA and into the pericardial cavity surrounding the heart.

FIG. 7 illustrates the further advancement of the inner catheter through the pericardial cavity and into a region adjacent to the xiphisternum.

FIG. 8A illustrates the inner catheter being "pulled out" and exteriorized by way of electromagnetic forces.

FIG. 9 shows the deployment of the closure device being advanced over the exteriorized inner catheter and to the exterior of the LAA ostium.

FIG. 9 illustrates the deployment of the closure device being deployed over the exterior of the LAA ostium without creating a puckering of the LAA ostium.

FIG. 12 illustrates the injury of the inner surface of the LAA prior to closure, where the injury causes an injury response which results in a more complete sealing along the opposed tissue surfaces.

FIG. 19 illustrates the accentuation of the waist of the LAA ostium and the wall of the proximal portion of the LAA caused by the inflation of the non-compliant balloon.

DETAILED DESCRIPTION OF THE INVENTION

Figure 1:
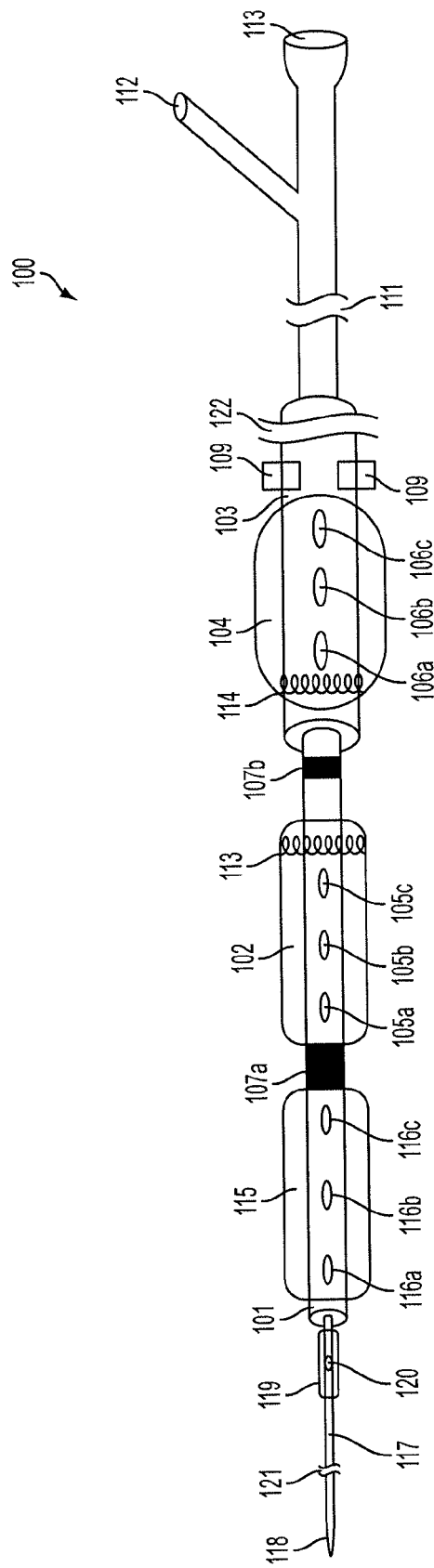
FIG. 1 is a perspective view of an exemplary embodiment of a catheter, which is part of present invention's system for accessing a pericardial space and preventing strokes arising from the LAA.

FIG. 1 is a perspective view of an exemplary embodiment of a catheter 100, which is part of the present invention's system for accessing a pericardial space and preventing strokes arising from the LAA. The present invention's system also includes closure device 1300, as shown in the exemplary embodiment of FIG. 13. FIG. 1 shows a stand-alone catheter 100 before it is introduced into a body cavity and thus, FIG. 1 shows inflatable balloons 102, 104, 115 and 119 in their un-inflated form. Inflatable balloon 104 is attached to an outer sheath 103. Inflatable balloons 104 and 115 are attached to inner sheath 101. Inflatable balloon 119 is attached to inner catheter 117. Depending on the desired degree of compliance, inflatable balloons 102, 104, 115 and 119 can be made of rubber, latex, polyisoprene, silicone, polyurethane, or any combination thereof. Rubber, latex, polyisoprene, and silicone produce more compliant inflatable balloons. Polyurethane produces non-compliant inflatable balloons. For non-compliant balloons, a higher pressure is ideal when inflating such balloons. A mixture of silicone and polyurethane produces half-way compliant inflatable balloons.

Figure 4:
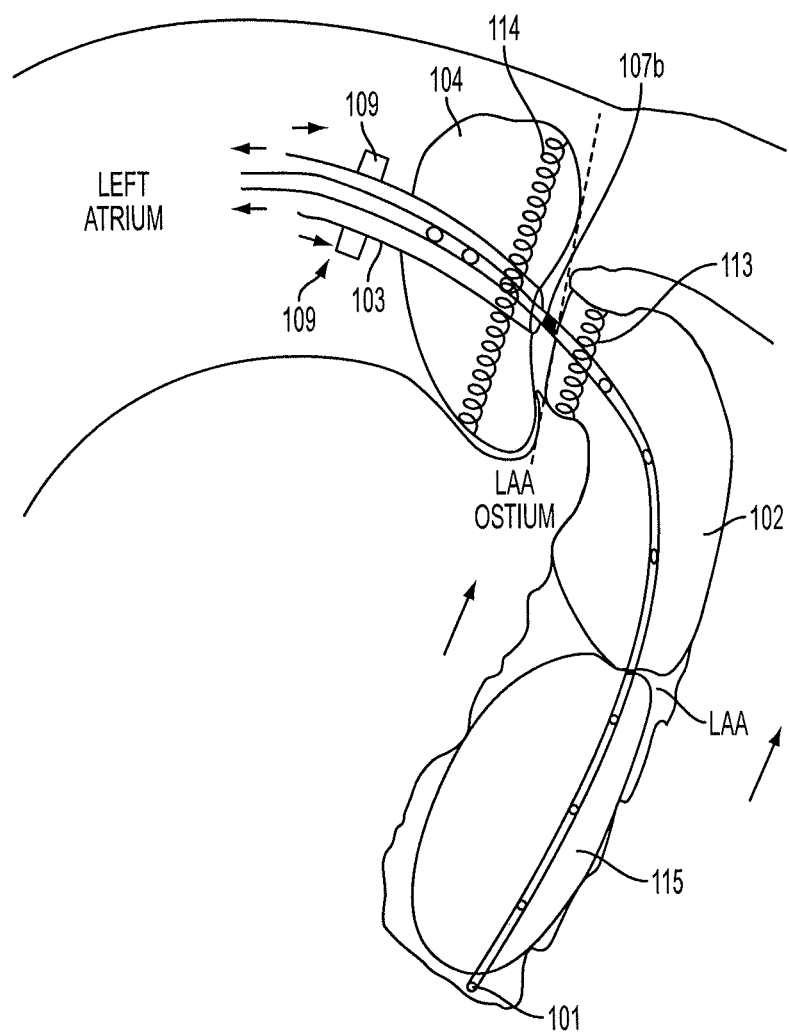
FIG. 4 is a first perspective view depicting the initial steps of the exemplary embodiment of FIG. 3.

A more compliant balloon will assume the contours of its surroundings when inflated. By contrast, a non-compliant balloon will expand the contours of its surroundings when inflated. In this exemplary embodiment of FIG. 1, inflatable balloons 104 and 115 are more compliant and thus, when inflated, each assumes the contours of its surroundings, as shown in FIG. 4. Thus, inflated balloon 104 will assume the shape of the smooth-walled left atrial cavity, whereas inflated balloon 115 will assume the shape of the rough-walled LAA. In particular, inflated balloon 115 can cover the potential sites of tear and bleeding, such as the lobes and recesses within the LAA walls.

Figure 19:
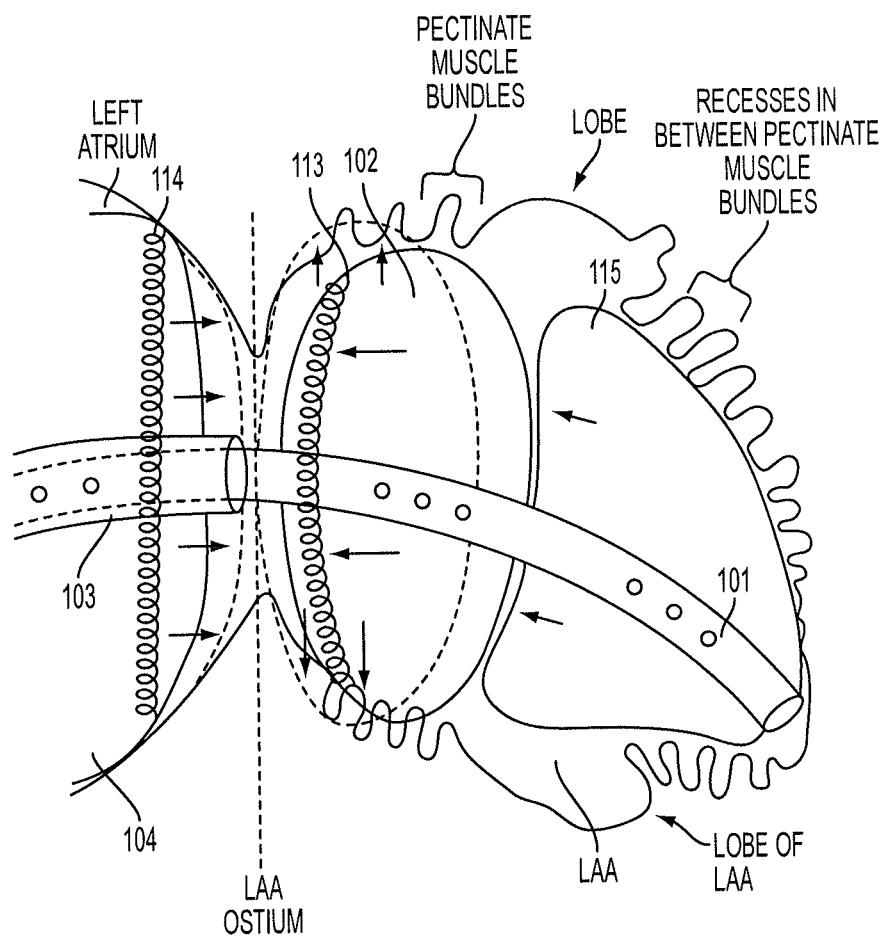
FIG. 19 is a tenth perspective view depicting the intermediate steps of the exemplary embodiment of FIG. 3, and in particular.

By contrast, inflatable balloon 102 is non-compliant and thus, when inflated, it expands the contours of its surrounding. As shown in FIG. 4, an inflated balloon 102 expands the contours of the LAA wall. By expanding the contours of its surroundings, inflatable balloon 102 accentuates the waist of the LAA ostium and the walls of the proximal portions of the LAA, as shown in FIG. 19. The ability of inflatable balloon 102 to accentuate the waist of the LAA ostium is an important feature because it prevents inflatable balloon 102 from falling into the left atrial cavity, which is particularly important because a distinct constriction is often absent at the LAA ostium. The application of electromagnetic forces will also result in inflated balloon 104 making a better contact with the smooth-wall left atrium cavity wall. Moreover, the ability of inflatable balloon to accentuate the LAA walls also helps cover the potential sites of tear and bleeding, such as the lobes and recesses within the LAA walls.

Optionally, inflatable balloons 102 and 115 can each have biocompatible hydrogel coated to its exterior (not illustrated in FIG. 1). Biocompatible hydrogel expands upon contact with fluid, such as blood or water. By absorbing the surrounding fluid, such as blood, the hydrogel helps to inhibit bleeding from the left atrium to the pericardial cavity, or from the LAA into the pericardial cavity. Alternatively, inflatable balloons 102 and 115 can each have sponges attached to its exterior (not illustrated in FIG. 1). The sponges will expand upon contact with fluid, such as blood or water. Like the hydrogel, the purpose of the sponges is to absorb surrounding fluid, such as blood, thereby inhibiting bleeding from the left atrium to the pericardial cavity, or from the LAA into the pericardial cavity Inflatable balloon 119 serves to anchor the LAA while (a) a closure device is being deployed to the LAA, and (b) the deflation of the inflated balloons if desired. Hence, inflatable balloon 119 can be termed the anchoring balloon.

Figure 20:
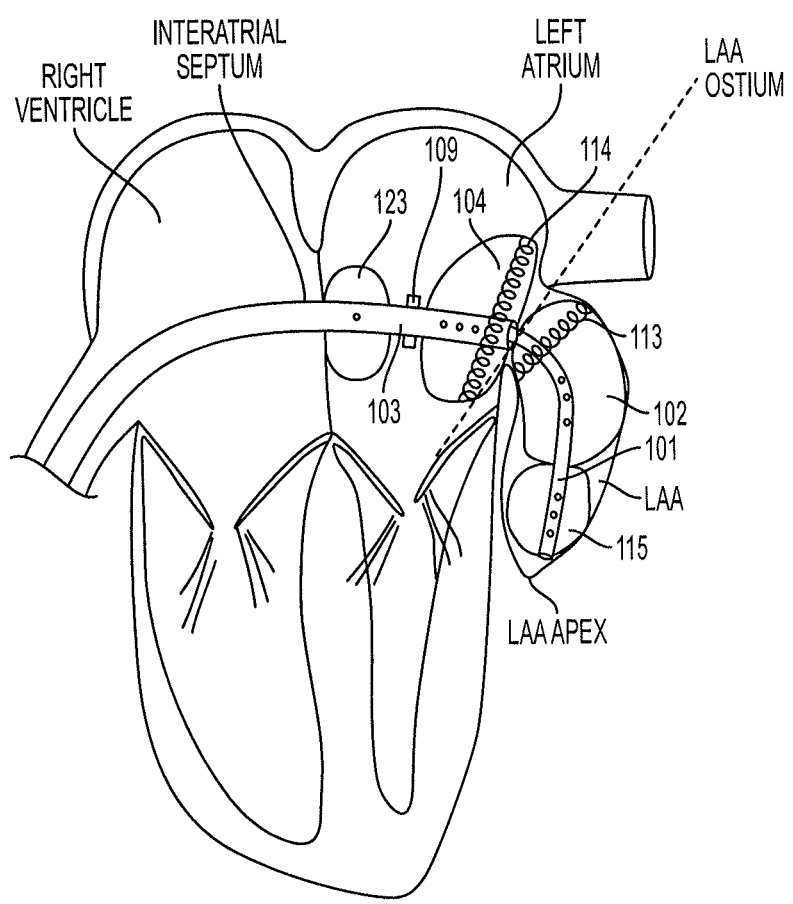
FIG. 20 is a perspective view depicting an optional step of the exemplary embodiment of FIG. 3.

Optionally, an additional inflatable balloon can be attached to the distal end of outer sheath 103 (not shown in FIG. 1). This additional inflatable balloon serves as an anchor and thus, is similar to inflatable balloon 119. This additional anchoring balloon prevents outer sheath 103 from being pulled back, and thus, keeps inflatable balloon 104 in-place. As shown in FIG. 20, this additional anchoring balloon can be inflated adjacent to the *fossa ovalis* or the interatrial septum, as shown in FIG. 20.

Despite the foregoing, it is contemplated that inflatable balloons 102, 104, 115 and 119 can each be compliant, semi-compliant, non-compliant, or any combination of the foregoing, depending on design needs. Additionally, it is contemplated that catheter 100 can be made up of more than four inflatable balloons depending on design needs.

Inflatable balloon 104 can be inflated with the input of air, or a suitable liquid material, such as saline, via inflation port 112 through outer sheath openings 106a, 106b, and 106c. Optionally, the suitable liquid material can be mixed with radiopaque contrast to provide spatial guidance. It is contemplated that the number of outer sheath openings can vary depending on design needs. For example, inflatable balloon 104 can be inflated via inflation port 112 through only one outer sheath opening, or through more than three outer sheath openings.

Inflatable balloons 102 and 115 can each be inflated with the input of air, or a suitable liquid material, such as saline, via inflation port 112 through inner sheath openings 105a, 105b, and 105c, and 116a, 116b, and 116c, respectively. Optionally, the suitable liquid material can be mixed with radiopaque contrast to provide spatial guidance. It is contemplated that the number of inner sheath openings can vary depending on design needs. For example, inflatable balloons 102 and 115 can each be inflated via inflation port 112 through only one inner sheath opening, or through more than three inner sheath openings.

Inflatable balloon 119 can be inflated with the input of air, or a suitable liquid material, such as saline, via inflation port 112 through inner catheter opening 120. Optionally, the suitable liquid material can be mixed with radiopaque contrast to provide spatial guidance. It is contemplated that the number of catheter openings can vary depending on design needs. For example, inflatable balloon 119 can be inflated via inflation port 112 through more than one inner catheter opening.

Inflation port 212 provides the portal for the input of air by, or a suitable liquid material, such as saline, by, for example, a balloon catheter inflation device commonly known to one skilled in the art. Optionally, the suitable liquid material can be mixed with radiopaque contrast to provide spatial guidance.

When inflated, inflatable balloon 104 has a larger diameter than that of the LAA ostium, as shown in FIG. 4. By having a larger diameter than that of the LAA ostium, inflatable balloon 104 is able to form an effective hemostatic seal, and effectively occlude the LAA ostium. Optionally, inflatable balloon 104 can have caliber tubes attached to its exterior. These tubes will allow for the application of vacuum or suction forces to the left atrial tissue to provide for a tighter hemostatic seal.

Optionally, catheter 100 can include electromagnetic coils. Electromagnetic coils can provide further support for firmly occluding the LAA ostium. In this exemplary embodiment of FIG. 1, electromagnetic coils 114 are located within inflatable balloon 103, and electromagnetic coils 113 are located within inflatable balloon 102. When inflatable balloons 103 and 102 are inflated, electromagnetic coils 113 and 114 also expand within the respective balloon, as shown in FIG. 4. Electromagnetic coils 113 and 114 are insulated wires coiled together to form a solenoid, and thus, can be made out of copper or any other metallic wire capable of conducting electricity.

The distal end of inner catheter 117 has tissue-penetrating tip 118 adapted to penetrate the LAA wall and the pericardial sac. Tissue-penetrating tip 118 can be a blunt or sharpened tip, and/or an RF electrode delivering RF current, to puncture the LAA wall tissue and optionally the pericardial sac tissue when optionally advanced out of the pericardial space as described below.

Optionally, the distal end of inner catheter 117 may include an electromagnetic element. This electromagnetic element interacts with an electromagnetic probe adapted to draw inner catheter 117 out of the pericardial cavity.

As duly noted by elongation identifier 121, the length of inner catheter 117 can vary depending on the body cavity dimension of the particular patient. As duly noted by elongation identifier 111, the length of inner sheath 101 can vary depending on the body cavity dimensions of the particular patient. Similarly, as duly noted by elongation identifier 122, the length of outer sheath 103 can vary depending on the body cavity dimensions of the particular patient.

Figure 2:
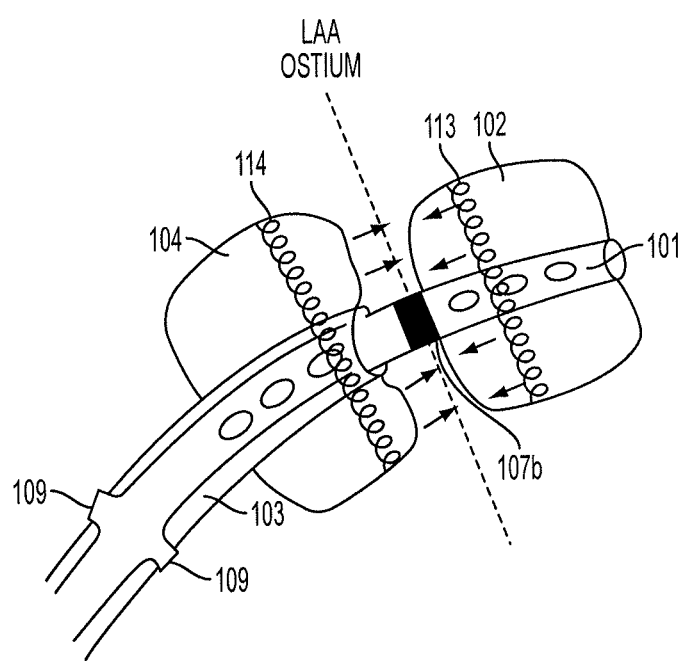
FIG. 2 is a perspective view of the locking means of the exemplary embodiment of FIG. 1.

Optionally, catheter 100 can include radiopaque marker bands. As shown in the exemplary embodiment of FIG. 1, radiopaque marker bands 107a and 107b are thin metal tubes placed along inner sheath 101 to provide spatial guidance under an X-ray fluoroscope. Inner sheath 101 is introduced into the body cavity, and advanced until radiopaque marker band 107b reaches the mid-point of the LAA ostium, as shown in FIG. 2. When radiopaque marker band 107b reaches the mid-point of the LAA ostium, inflatable balloon 102 is inflated. Moreover, radiopaque marker band 107b provides guidance for advancing outer sheath 103. In particular, outer sheath 103 is introduced into the body cavity and advanced through the body cavity until outer sheath 103 reaches radiopaque marker band 107b.

After balloons 102, 103, and 115 are inflated, locking means 109 is activated. Locking means 109 is shown in FIG. 2. Locking means 109 is a spring-loaded device housed in inner sheath 101 that, upon activation, the protrusions would bulge out through the corresponding protrusion slots on outer sheath 103, as shown in FIG. 2. These protrusions and corresponding protrusion slots can be of varying dimensions. The purpose of locking means 109 is to render stationary inflated balloons 102 and 104 so that the hemostatic seal is firmly occluding the LAA ostium.

Optionally, an additional locking mechanism similar to locking means 109 can be present on outer sheath 103 (not illustrated in FIG. 1). This additional locking mechanism would be used to render stationary (a) an additional anchoring balloon inflated within the left atrium adjacent to the interatrial septum, and (b) outer sheath 103. Like locking mechanism 109, this additional locking mechanism would be a spring-loaded device housed in inner sheath 101 that, upon activation, the protrusions would bulge out through the corresponding protrusion slots on outer sheath 103, as shown in FIG. 2. These protrusions and corresponding protrusion slots can be of varying dimensions.

Control port 113 provides the portal for connection to catheter handling devices designed to control and navigate inner sheath 101, outer sheath 103, and inner catheter 117 to the desired locations. Inner sheath 101, outer sheath 103, and inner catheter 117 can also be steerable such that each are deflectable with pull wire technology or other methods to allow for the respective tips to be deformed in the desired direction.

FIG. 2 is a perspective view of the locking means in the exemplary embodiment of FIG. 1. Locking means 109 is a spring-loaded device housed in inner sheath 101 that, upon activation, the protrusions would bulge out through the corresponding protrusion slots on outer sheath 103. These protrusions and corresponding protrusion slots can be of varying dimensions. The purpose of locking means 109 is to render stationary inflated balloons 102 and 104 so that the hemostatic seal is firmly occluding the LAA ostium.

Figure 3:
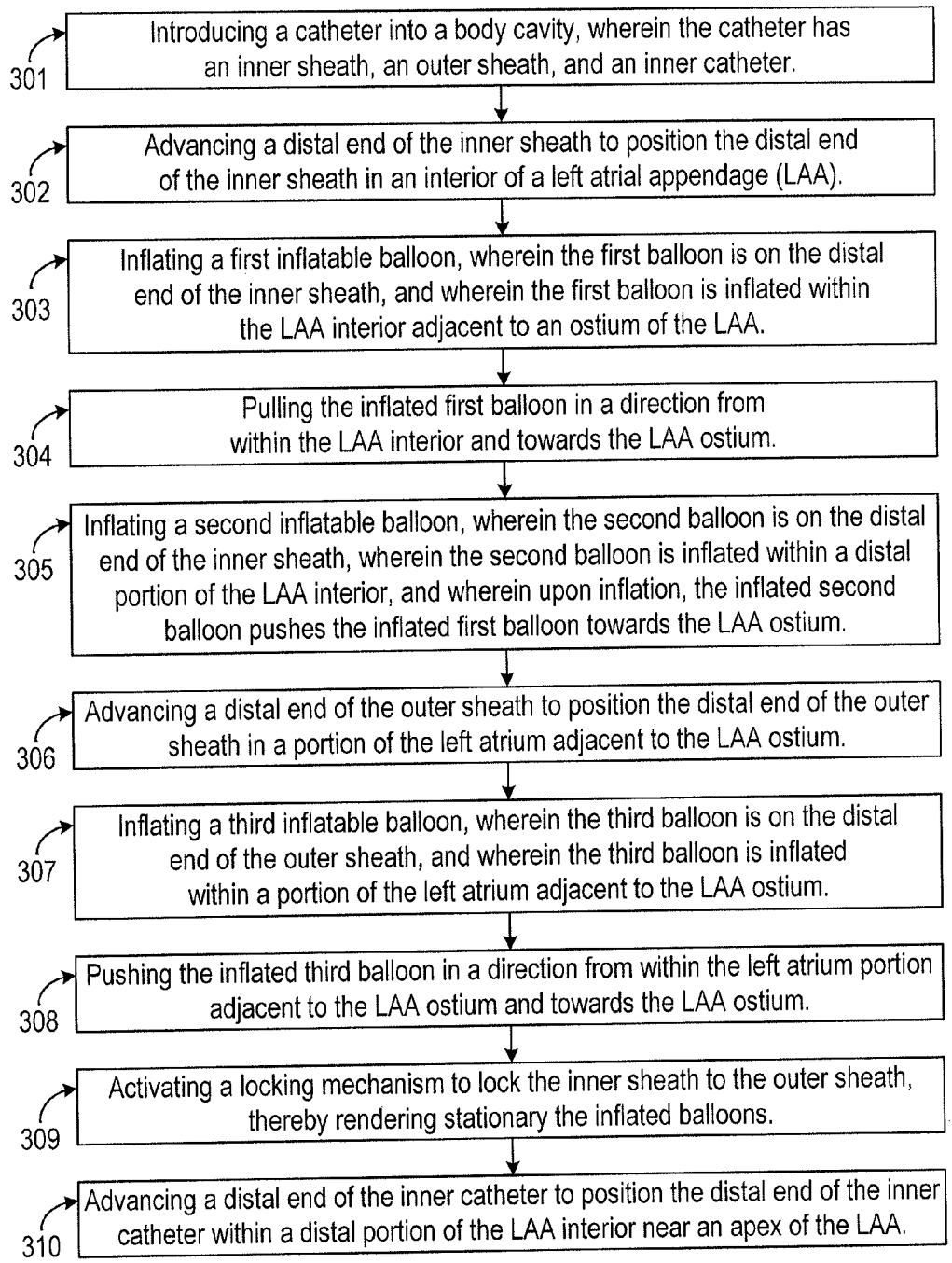
FIG. 3 is a flowchart depicting an exemplary embodiment of the present invention's method for accessing a pericardial space and preventing strokes arising from the LAA.
Figure 5:
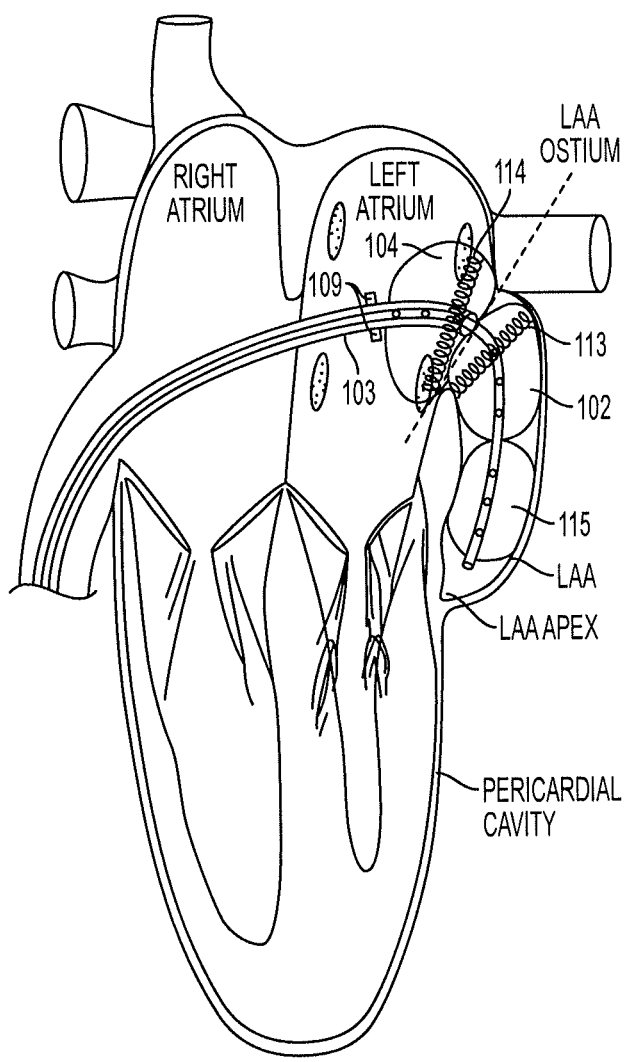
FIG. 5 is a second perspective view depicting the initial steps of the exemplary embodiment of FIG. 3.
Figure 6:
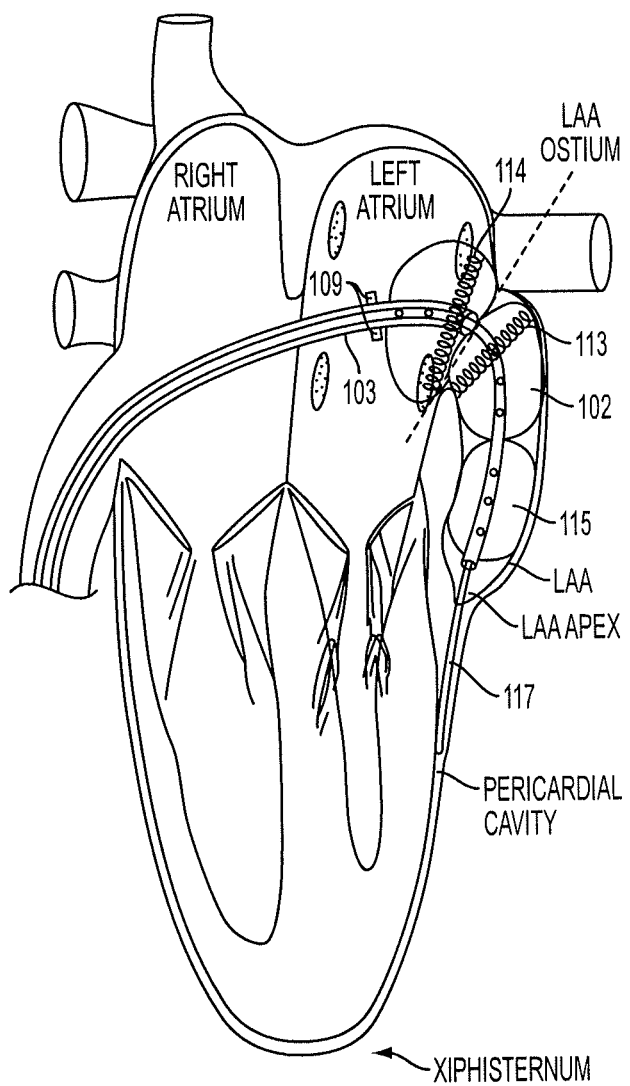
FIG. 6 is a third perspective view depicting the intermediate steps of the exemplary embodiment of FIG. 3, and in particular.
Figure 7:
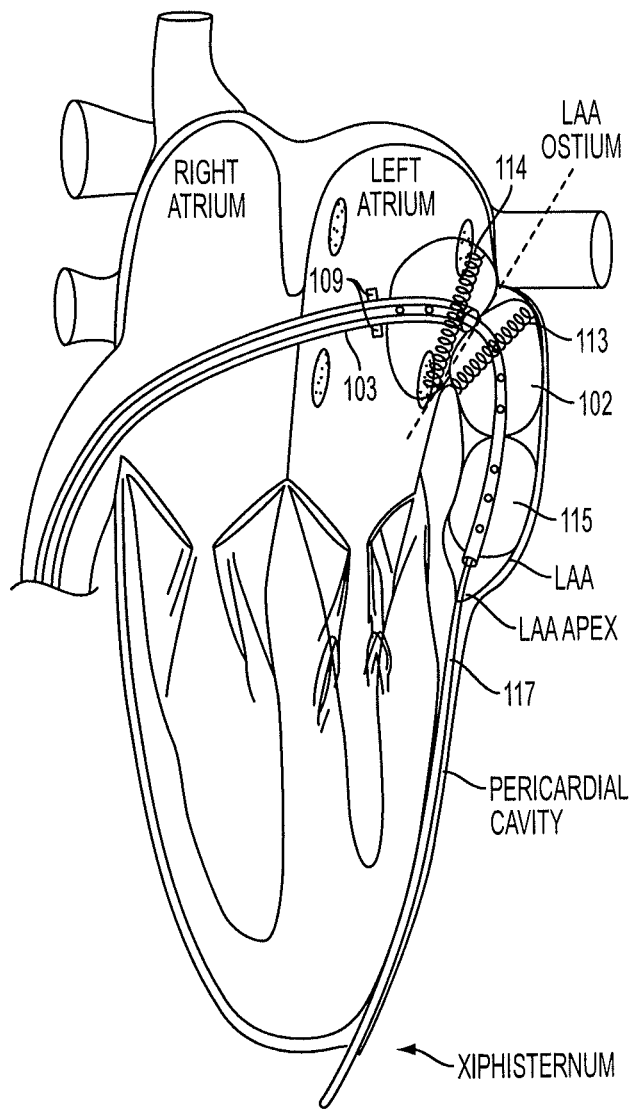
FIG. 7 is a fourth perspective view depicting the intermediate steps of the exemplary embodiment of FIG. 3, and in particular.

FIG. 3 is a flowchart depicting an exemplary embodiment of the present invention's method for accessing a pericardial space and preventing strokes arising from the LAA. At step 301, catheter 100 is introduced into a body cavity. Typically, catheter 100 can be introduced in the body cavity via a puncture. Catheter 100 can be introduced into different body cavities, such as via a femoral vein, a jugular vein, an axillary vein, or a subclavian vein. Alternatively, catheter 100 can also be introduced directly into the chambers of the heart via introduction at the right atrium and advanced to the left atrium, as shown in FIGS. 5-7. In yet another embodiment, catheter 100 can be introduced directly into the chambers of the heart via introduction at the apex of the left ventricle. As shown in FIG. 1, catheter 100 comprises inner sheath 101, outer sheath 103, and inner catheter 117, among other components.

At step 302, inner sheath 101 is advanced to position a distal end of inner sheath 101 within an interior of the LAA. As shown in FIGS. 4-5, inner sheath 101 can be advanced to position its distal end within the LAA interior via a left atrium. Inner sheath 101 (as well as outer sheath 103 at step 306 and inner catheter at step 310) may be advanced to the left atrium by any known technique, including transseptal delivery where the left atrium is accessed from the right atrium, thorascopic delivery, via a retrograde transaortic approach, and the like. Optionally, catheter 100 may comprise radiopaque marker bands, such as radiopaque marker band 107a and 107b, which can provide spatial guidance for positioning the distal end of inner sheath 101 within the LAA interior.

Figure 16:
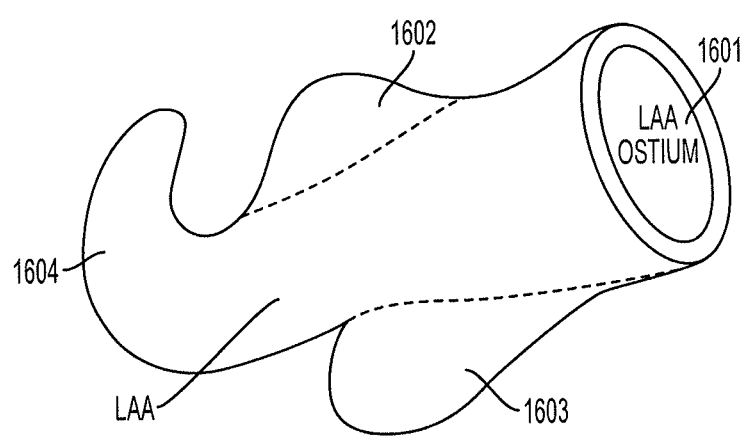
FIG. 16 is an exemplary depiction of an LAA showing the presence of distinct protrusions within the LAA termed lobes.
Figure 18:
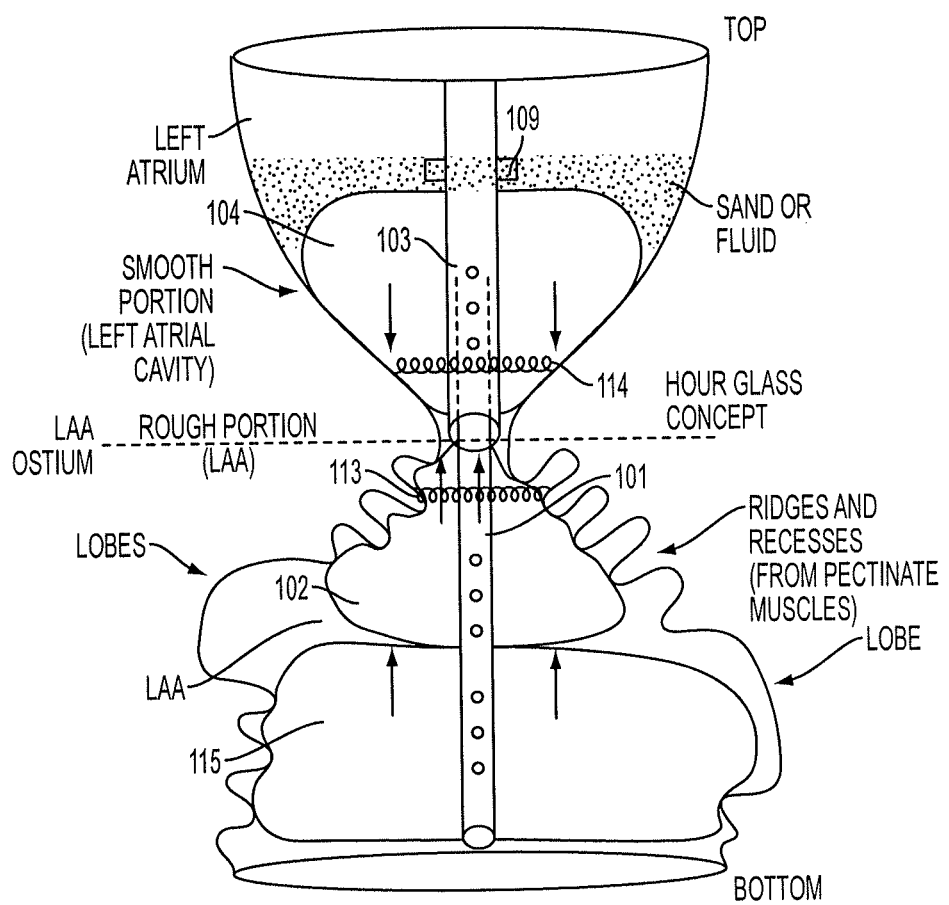
FIG. 18 is another exemplary depiction of an LAA in accordance with the hour-glass concept.

At step 303, inflatable balloon 102 is inflated within an interior of the LAA adjacent to the LAA ostium, as shown in FIG. 4. Inflatable balloon 102 can be inflated with the input of air, or a suitable liquid material, such as saline, via inflation port 112 through inner sheath openings 105a, 105b, and 105c. Optionally, the suitable liquid material can be mixed with radiopaque contrast to provide spatial guidance. Inflatable balloon 102 is inflated with high occlusive pressures because it is a non-compliant balloon. Because inflatable balloon 102 is non-compliant, it expands the contours of its surrounding when inflated. The LAA is distensible and hence should readily deform in response to high pressure inflation with non-compliant balloon 102. Thus, as shown in FIG. 19, non-compliant balloon 102 accentuates the waist of the LAA interior adjacent to the LAA ostium to prevent an inflated non-compliant balloon 102 from falling into the left atrium, which is particularly important because a distinct constriction is often absent at the LAA ostium. Additionally, due to the presence of deep crypts or recesses in-between the pectinate muscles and the presence of protrusions or lobes in the LAA interior, as shown in FIGS. 16, 18-19, an inflated non-compliant balloon 102 also accentuates these crypts, recesses, protrusions, and lobes. Therefore by expanding the contours of its surroundings in the LAA interior, non-compliant balloon creates a more effective hemostatic seal circumferentially about the LAA ostium. This hemostatic seal inhibits bleeding from the left atrium into the pericardial cavity. Optionally, the presence of this hemostatic seal can be confirmed (step not illustrated) with a test injection of contrast from the tip of inner sheath 101 to ensure that the contrast injected into the LAA does not flow back into the left atrium.

Optionally, another embodiment of this method may include a set of electromagnetic coils 113 located within inflatable balloon 102, and a set of electromagnetic coils 114 located within inflatable balloon 104. Thus, when balloons 102 and 104 are inflated, electromagnetic coils 113 and 114 also expand within the respective balloon, respectively. By way of electromagnetic forces created by these electromagnetic coils, inflated balloon 102 is pulled towards the LAA ostium by electromagnetic coils 114. Conversely, inflated balloon 104 is pulled towards the LAA ostium by electromagnetic coils 113. Thus, these electromagnetic forces promote attraction between inflated balloons 102 and 104, thereby further enhancing the hemostatic seal circumferentially about the LAA ostium.

At step 304, inflated balloon 102 is pulled in a direction from within the LAA interior and towards to the LAA ostium to occlude the LAA ostium. Inflated balloon 102 can be pulled in a direction from within the LAA interior and towards to the LAA ostium by pulling on inner sheath 102 in the same direction.

At step 305, inflatable balloon 115 is inflated within a distal portion of the LAA interior, as shown in FIGS. 4 and 19. Inflatable balloon 115 can be inflated with the input of air, or a suitable liquid material, such as saline, via inflation port 112 through inner sheath openings 116a, 116b, and 116c. Optionally, the suitable liquid material can be mixed with radiopaque contrast to provide spatial guidance. Inflatable balloon 115 is more compliant and thus, when inflated, it assumes the contours of its surroundings, as shown in FIGS. 4 and 19. By assuming the contours of its surroundings in the LAA, inflated balloon 115 seals the potential sites for tear or perforation in the LAA wall, thereby inhibiting bleeding (a) from the left atrium into the pericardial cavity, and (b) from the LAA into the pericardial cavity. Additionally, due to the presence of deep crypts or recesses in-between the pectinate muscles and the presence of protrusions or lobes in the LAA interior, as shown in FIGS. 16, 18-19, an inflated balloon 115 also covers these crypts, recesses, protrusions, and lobes. Furthermore, inflated balloon 115 pushes inflated balloon 102 towards the LAA ostium.

Optionally, inflatable balloons 102 and 115 can each have biocompatible hydrogel coated to its exterior (step not illustrated in FIG. 3). Biocompatible hydrogel expands upon contact with fluid, such as blood or water. By absorbing the surrounding fluid, such as blood, the hydrogel helps to inhibit bleeding from the left atrium to the pericardial cavity, or from the LAA into the pericardial cavity. Alternatively, inflatable balloons 102 and 115 can each have sponges attached to its exterior (step not illustrated in FIG. 3). The sponges will expand upon contact with fluid, such as blood or water. Like the hydrogel, the purpose of the sponges is to absorb surrounding fluid, such as blood, thereby inhibiting bleeding from the left atrium to the pericardial cavity, or from the LAA into the pericardial cavity At step 306, outer sheath 103 is advanced to position a distal end of outer sheath 103 in a portion of the left atrium adjacent to the LAA ostium, as shown in FIGS. 4 and 19.

At step 307, inflatable balloon 104 is inflated within a portion of the left atrium adjacent to the LAA ostium, as shown in FIGS. 4 and 19. Inflatable balloon 104 can be inflated with the input of air, or a suitable liquid material, such as saline, via inflation port 112 through outer sheath openings 106a, 106b, and 106c. Optionally, the suitable liquid material can also be mixed with radiopaque contrast. Unlike the LAA interior, the left atrium portion adjacent to the LAA ostium is smooth-walled. When inflated, balloon 104 has a larger diameter than that of the LAA ostium, as shown in FIG. 4. By having a larger diameter than that of the LAA ostium, inflated balloon 104 envelops the LAA ostium to firmly occlude the LAA ostium to create an effective hemostatic seal, thereby inhibiting bleeding from the left atrium into the pericardial cavity. Additionally, inflated balloon 104 prevents inflated balloon 102 from falling into the left atrium and thus, inflated balloon 104 helps render stationary inflated balloon 102 within the LAA interior.

At step 308, inflated balloon 104 is pushed in a direction from within the left atrium portion adjacent to the LAA ostium and towards the LAA ostium. Inflated balloon 104 can be pushed in a direction from within the left atrium portion adjacent to the LAA ostium and towards the LAA ostium by pushing the outer sheath in the same direction. As a result, inflated balloon 104 occludes the LAA ostium more firmly to create an effective hemostatic seal, thereby inhibiting bleeding from the left atrium into the pericardial cavity. Additionally, inflated balloon 104 prevents inflated balloon 102 from falling into the left atrium and thus, inflated balloon 104 helps render stationary inflated balloon 102 within the LAA interior.

Optionally, inflated balloon 104 has caliber tubes attached to its exterior (step not shown in FIG. 3). These tubes will allow for the application of vacuum or suction forces to the left atrial tissue to provide for a tighter hemostatic seal.

At step 309, locking means 109 is activated. Locking means 109 is a spring-loaded device housed in inner sheath 101 that, upon activation, the protrusions would bulge out through the corresponding protrusion slots on outer sheath 103. These protrusions and corresponding protrusion slots can be of varying dimensions. The purpose of locking means 109 is to render stationary inflated balloons 102 and 104 so that the hemostatic seal is firmly occluding the LAA ostium.

Optionally, another embodiment of this method may include an additionally step of inflating an additional inflatable balloon located on the outer sheath, as shown in FIG. 20. This additional inflatable balloon is inflated in a portion of the left atrium adjacent to the *fossa ovalis* or the interatrial septum, as shown in FIG. 20. This balloon serves as an anchor to render stationary inflated balloon 104. Optionally, an additional locking mechanism similar to locking means 109 can be present on outer sheath 103 (not illustrated in FIG. 1). This additional locking mechanism would be used to render stationary (a) an additional anchoring balloon inflated within the left atrium adjacent to the interatrial septum, and (b) outer sheath 103. Like locking mechanism 109, this additional locking mechanism would be a spring-loaded device housed in inner sheath 101 that, upon activation, the protrusions would bulge out through the corresponding protrusion slots on outer sheath 103, as shown in FIG. 2. These protrusions and corresponding protrusion slots can be of varying dimensions.

At step 310, inner catheter 117 is advanced to position a distal end of inner catheter 117 within a distal portion of the LAA interior near an apex of the LAA. As shown in FIG. 1, the distal end of inner catheter 117 comprises tissue-penetrating tip 118.

At step 311, tissue-penetrating tip 118 of inner catheter 117 punctures a wall of the LAA apex from within the LAA interior and into the pericardial cavity, as shown in FIG. 6. Tissue-penetrating tip 118 can be a blunt or sharpened tip, and can further comprise a RF electrode delivering RF current sufficient to puncture the LAA wall tissue and the parietal pericardium. Upon puncturing the wall of the LAA apex, no significant blood will enter the pericardial cavity because of the tight hemostatic seal previously formed by the inflated balloons. After tissue-penetrating tip 118 punctures the LAA wall, the distal end of inner catheter 117 is advanced into the pericardial cavity, as shown in FIG. 6.

Figure 8A:
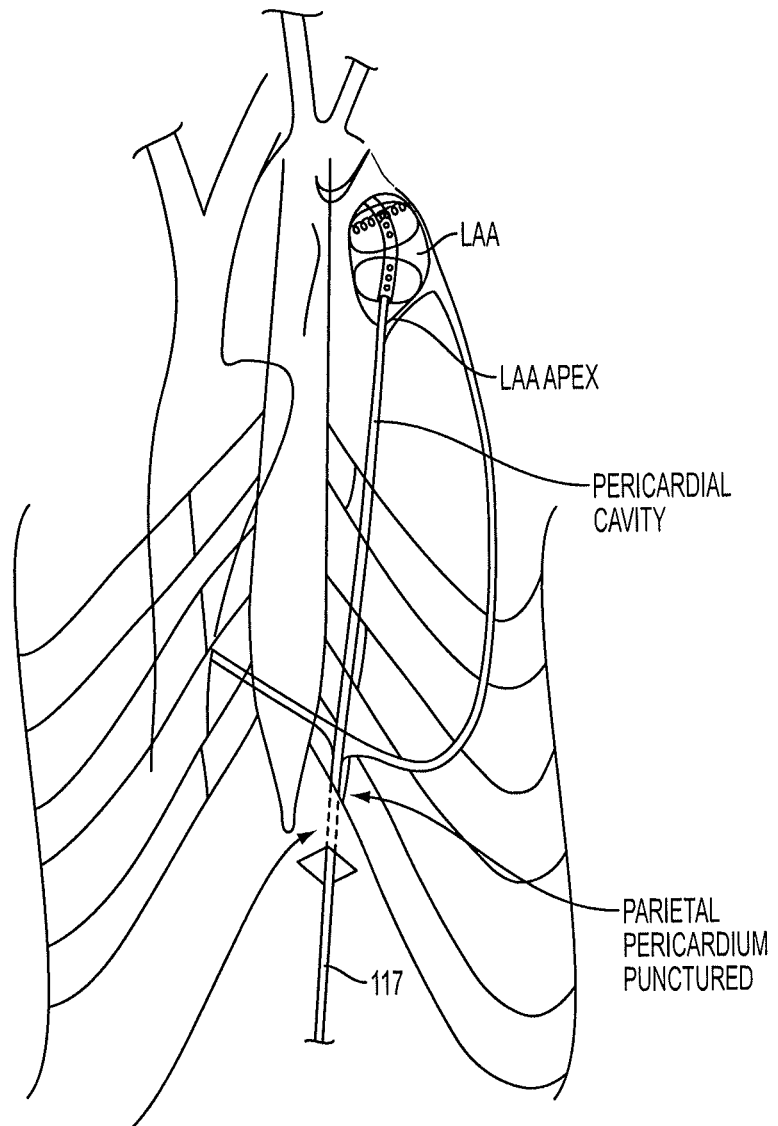
FIG. 8A is a fifth perspective view depicting the intermediate steps of the exemplary embodiment of FIG. 3, and in particular.
Figure 8B:
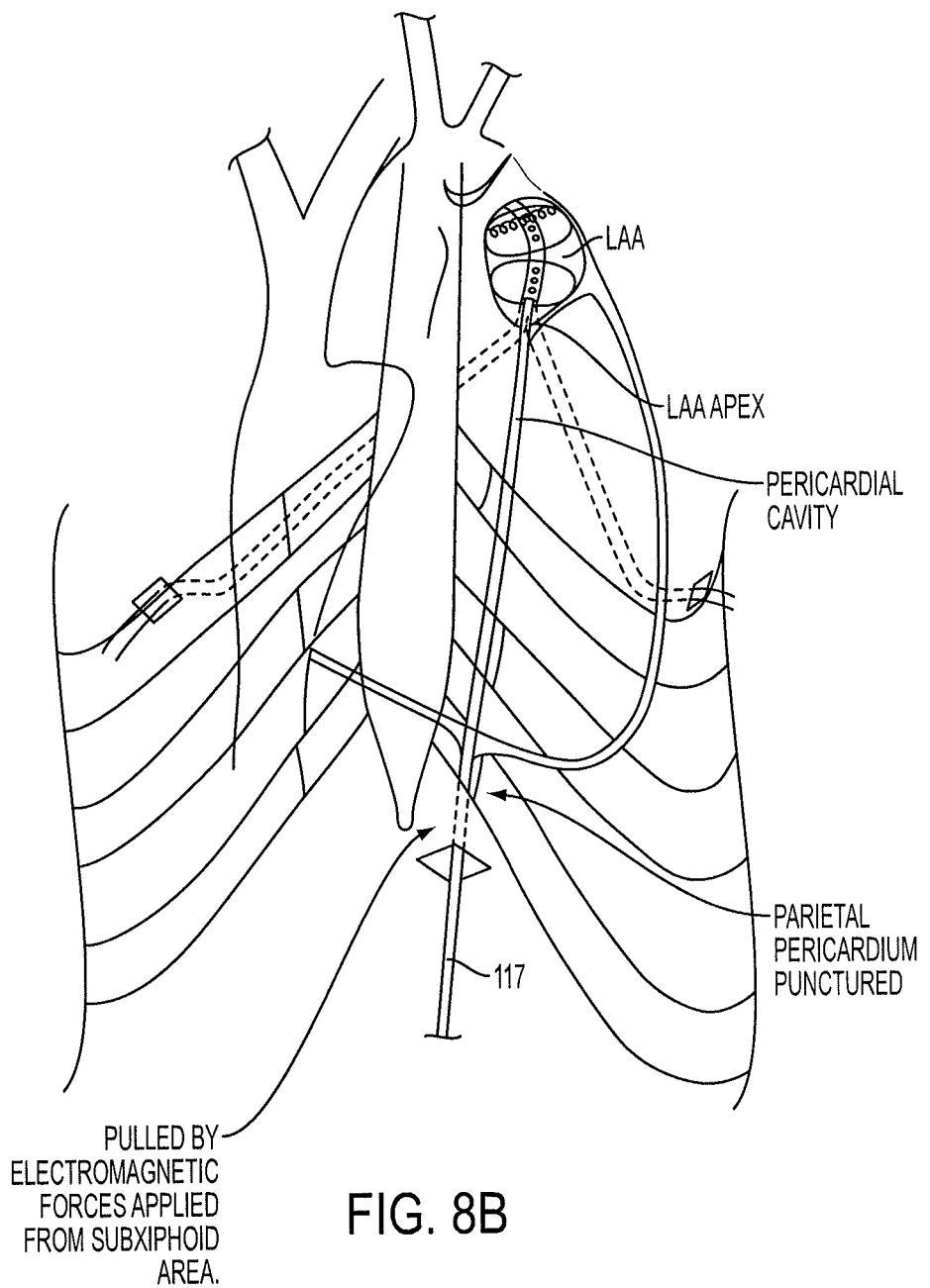
FIG. 8B illustrates alternative sites for exteriorizing the inner catheter after it has been drawn from the pericardial cavity.

At step 312, the distal end of inner catheter 117 advances through the pericardial cavity, along the anterior surface of the ventricle, to a region adjacent to the sternum, and in particular, the xiphisternum, as shown in FIGS. 7-8A. The xiphisternum, also known as the xiphoid process, is the lowermost part of the sternum. Alternatively, inner catheter 117 can be advanced through the pericardial cavity to another site at which inner catheter 117 will be exteriorized. Other desired sites of exteriorization include the parietal pericardium in the right or left pectoral regions, as such as FIG. 8B. This will allow for insertion of the snare to ligate the LAA with an incision made in the skin over the intercostal space in the right or left pectoral regions (the desired site of exteriorization). Furthermore, other desired sites of exteriorization may include any other region higher up in the chest, lateral to the sternum between the ribs.

At step 313, when inner catheter 117 reaches the desired site of exteriorization, tissue-penetrating tip 118 punctures the wall of the pericardial cavity at this site. This wall of the pericardial cavity is also known as the parietal pericardium. The pericardial cavity is punctured from within the pericardial cavity in an outward direction at the desired site of exteriorization, and inner catheter 117 enters the subcutaneous tissues at the desired site of exteriorization. As shown in FIGS. 7-8A, a desired site of exteriorization is the region adjacent to the xiphisternum. Alternatively, as shown in FIG. 8B, other desired sites of exteriorization include the parietal pericardium in the right or left pectoral regions.

At step 314, inner catheter 117 is externalized or "pulled out" from the pericardial cavity with manual force, electromagnetic force, radio frequency energy delivery, or any combination thereof. For example, as shown in FIG. 8A, inner catheter 117 can be externalized from the pericardial cavity with electromagnetic forces applied with another catheter having an electromagnetic probe that is placed at the desired site of exteriorization. A small incision can be made in the skin to the left of the xiphisternum, or higher up in the chest for example, lateral to the sternum between the ribs. An electromagnetic probe is introduced towards the pericardial cavity through this incision to attract inner catheter 117 (that has electromagnets incorporated) that is then exteriorized. The distal end of inner catheter 117 may include an electromagnetic element, which interacts with the electromagnetic probe adapted to draw inner catheter 117 out of the pericardial cavity. Application of RF current may also be considered to draw inner catheter 117 out of the pericardial cavity.

Figure 14:
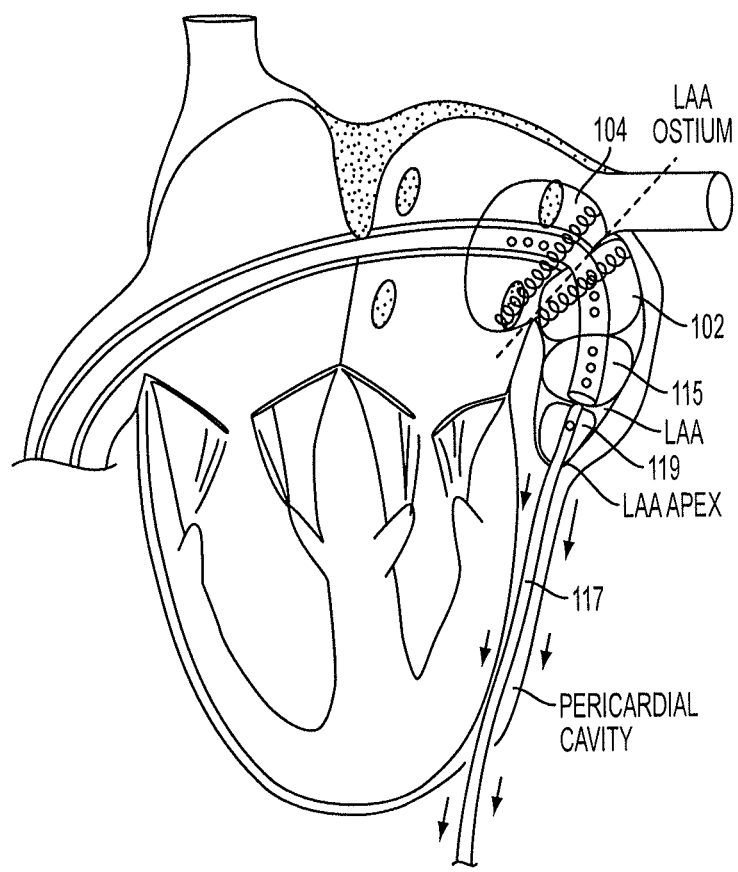
FIG. 14 is a ninth perspective view depicting the intermediate steps of the exemplary embodiment of FIG. 3.

At step 315, inner catheter 117 is advanced to position a proximal end of inner catheter 117 within the distal portion of the LAA interior near the LAA apex, as shown in FIG. 14.

At step 316, inflatable balloon 119 is inflated within the distal portion of the LAA interior near the LAA apex, as shown in FIG. 14. Inflatable balloon 119 can be inflated with the input of air, or a suitable liquid material, such as saline, via inflation port 112 through inner catheter opening 120. Optionally, the suitable liquid material can be mixed with radiopaque contrast to provide spatial guidance. Inflatable balloon 119 serves to anchor the LAA and hence, inflated balloon 119 can be termed the anchoring balloon.

At step 317, inflated balloon 119 is pulled in a direction from within the distal portion of the LAA interior near the LAA apex and towards the pericardial cavity to anchor the LAA. Inflated balloon 119 can be pulled in a direction from within the distal portion of the LAA interior near the LAA apex and towards the pericardial cavity by pulling inner catheter 117 in the same direction. This will serve to straighten the LAA (a structure than can be very tortuous in its course) and thus make it easier to (a) advance closure device 1300 over the exterior of the LAA, and (b) deflate the inflated balloons (step not illustrated).

Figure 9:
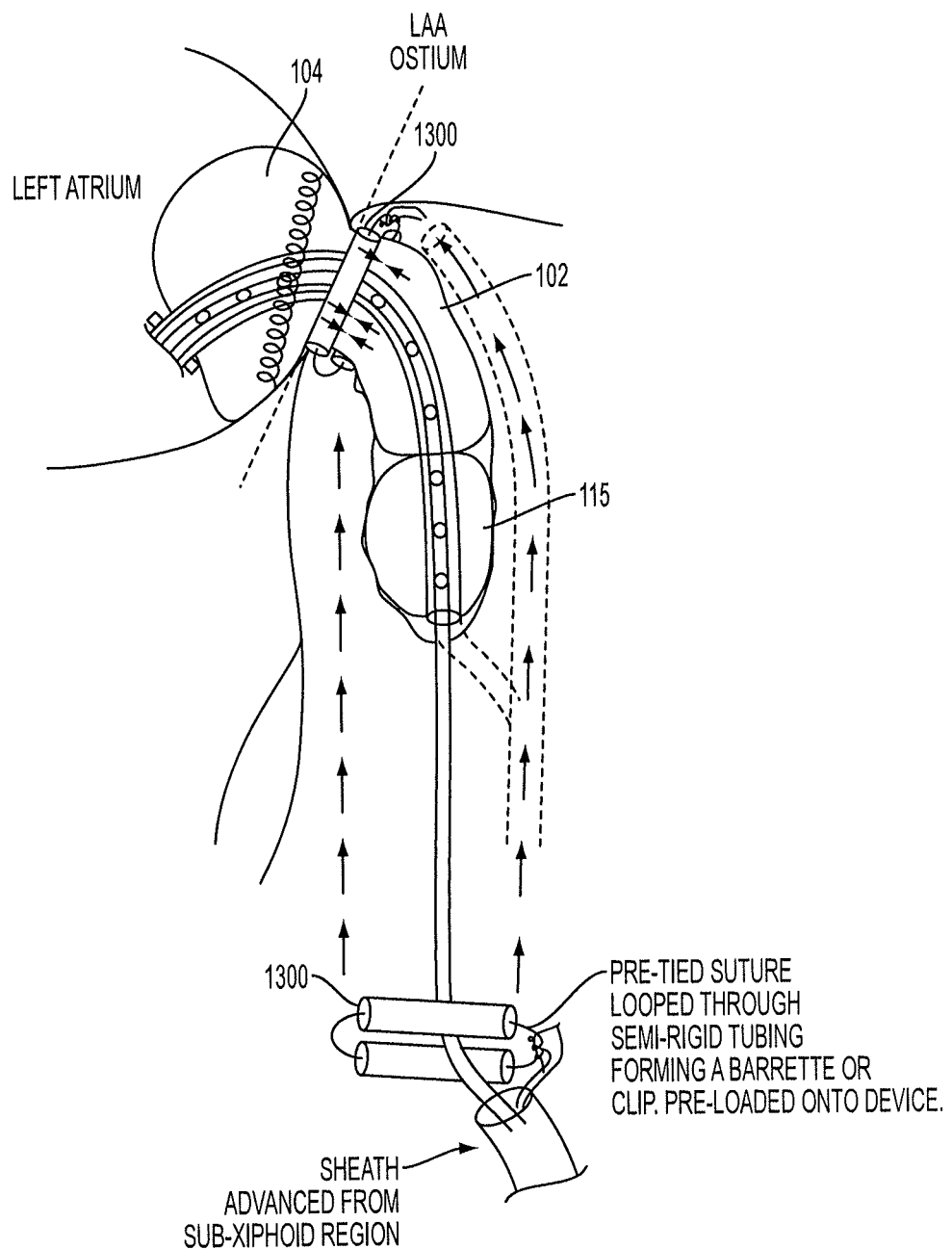
FIG. 9 is a sixth perspective view depicting the intermediate steps of the exemplary embodiment of FIG. 3, and in particular.

At step 318, the exteriorized inner catheter 117 is used as a rail over in which closure device 1300 is advanced to the LAA, and is advanced over the exterior of the LAA to a position overlying the LAA ostium so that closure will seal the interior of the LAA and isolate any clot from the left atrium, as shown in FIG. 9. Closure device 1300 is made up of suture 1301 looped through two semi-rigid hollow tubes 1302 and 1303 which can function as a "lasso" or a "snare," as shown in FIGS. 9 and 11-13.

Figure 11:
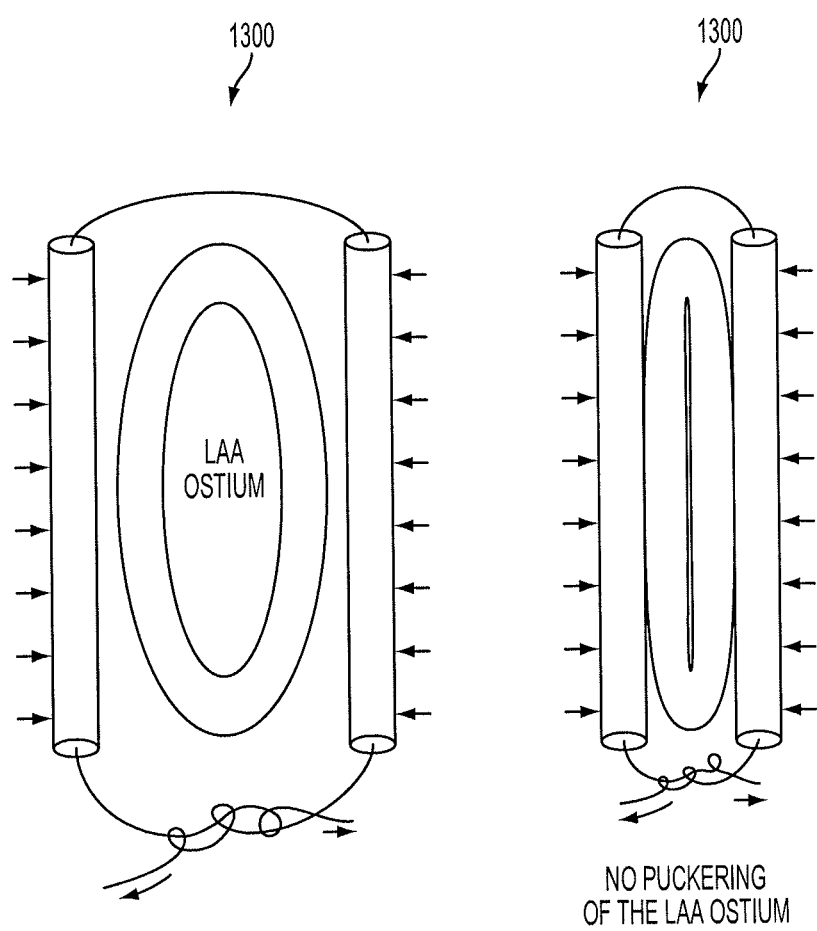
FIG. 11 is a seventh perspective view depicting the intermediate steps of the exemplary embodiment of FIG. 3, and in particular.
Figure 12:
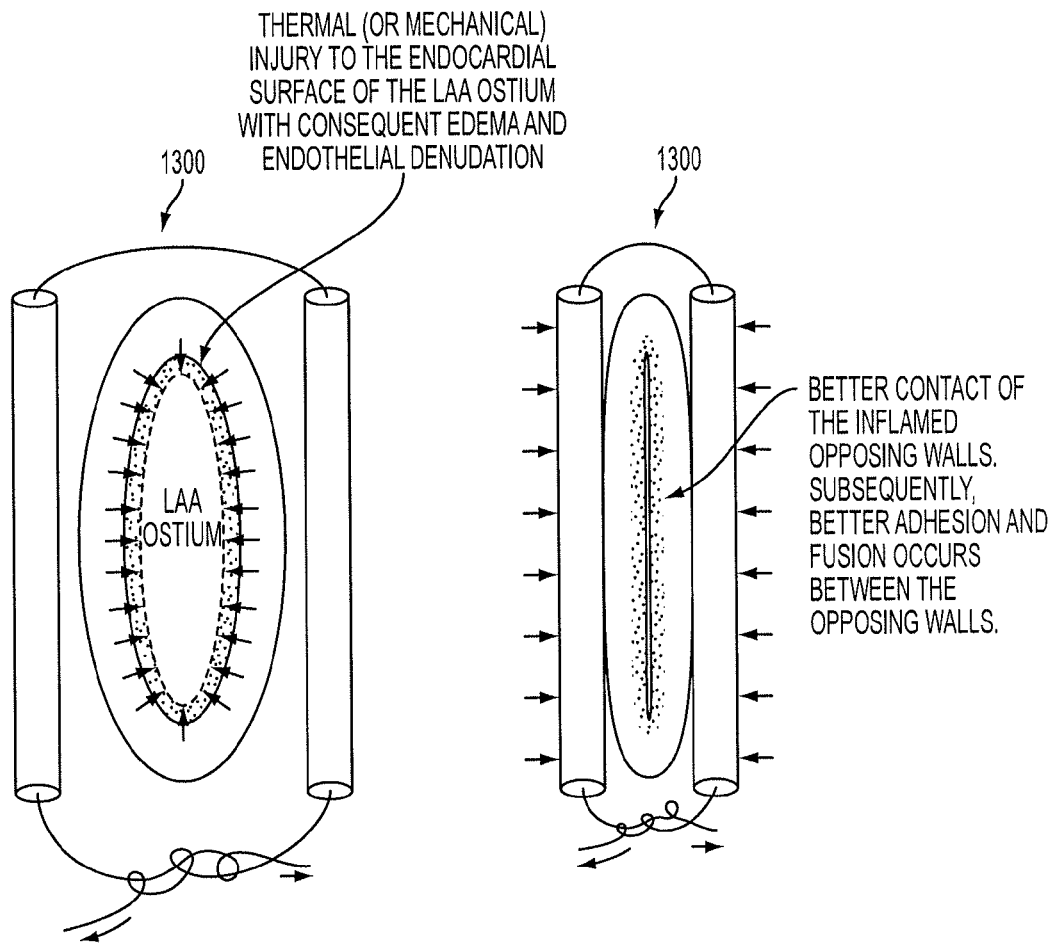
FIG. 12 is an eighth perspective view depicting the intermediate steps of the exemplary embodiment of FIG. 3, and in particular.
Figure 13:
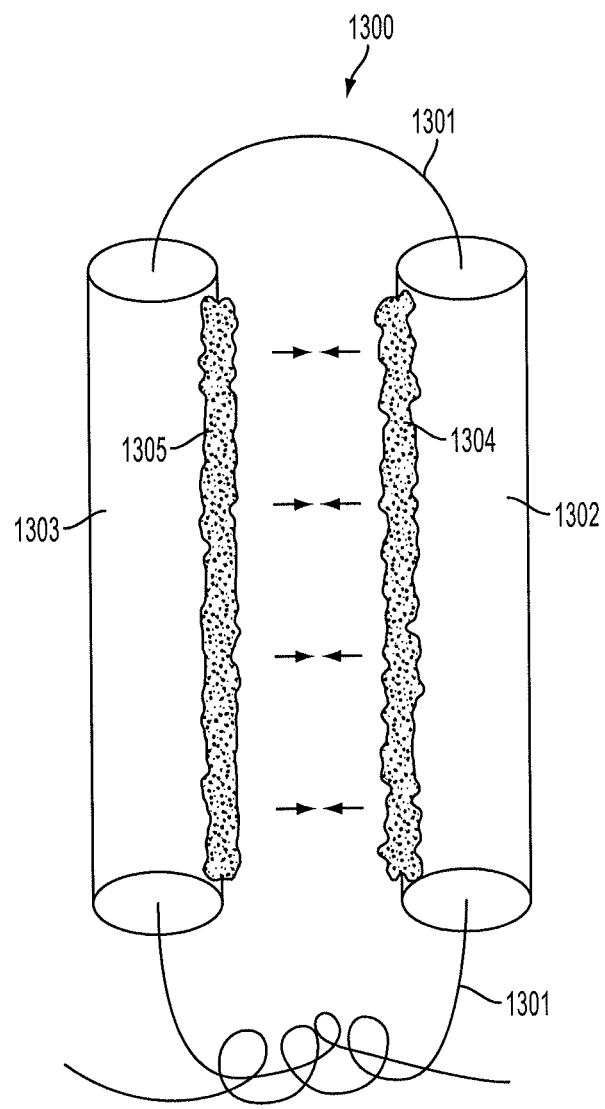
FIG. 13 illustrates the present invention's closure device, which is part of present invention's system for accessing a pericardial space and preventing strokes arising from the LAA.

At step 319, closure device 1300 is deployed over the exterior of the LAA ostium, as shown in FIGS. 9 and 11-13. Closure device 1300 is deployed over the exterior of the LAA ostium by position each of the semi-rigid hollow tubes along the short axis (or short diameter) of the exterior of the LAA ostium, and thereafter tightening the suture to seal the interior of the LAA ostium. As shown in FIG. 11, closure device 1300 applies forces along the short axis or short diameter of the oval or elliptical LAA ostium, thereby sealing the LAA ostium without a puckering effect. Optionally, as shown in FIG. 13, semi-rigid tubes 1302 and 1303 may be coated over at least an inner surface with a hydrogel, silicone gel, and/or other biocompatible material. Hydrogels will expand on contact with water or blood to further compress the LAA ostium.

At step 320, the endocardial surface of the interior of the LAA ostium is thermally or mechanically injured to induce a tissue response that enhances closure and sealing, as shown in FIG. 12. For example, thermal injury may be induced by circulating a hot fluid through inflated balloons 102 and 104 that are occluding the LAA ostium. Such injury may comprise delivering heat through inflated balloons 102 and 104 via circulation of externally heated liquids such as dextrose, glycine, saline, and glycerine, and thus creating conductive heating. Alternatively, the LAA tissue may be injured or fused by applying RF current through inflated balloons 102 and 104, and/or the external closure device. The RF current is delivered through inflated balloons 102 and 104 and/or closure device 1300, and creating resistive heating of the ostial tissues. Apposition of injured surfaces will cause "tissue welding," i.e. cross linking of the tissue collagen, resulting in a more complete closure. Other energy sources, such as high energy focused ultrasound, mechanical abrasion, laser or cryoablation, may also be used. The combination of pressure exerted by a clip or barrette and adhesions formed at the endocardial surface will exert a synergistic effect in ensuring that the occlusion at the LAA ostium is complete and persistent.

Optionally, after step 20 (steps not illustrated in FIG. 3), an alternative embodiment can further include the steps of: deflating the first inflated balloon, deflating the second inflated balloon, deflating the third inflated balloon, deactivating the locking mechanism, removing the outer sheath from the body cavity, and removing the inner sheath from the body cavity.

FIG. 4 is a first perspective view depicting the initial steps of the exemplary embodiment of FIG. 3.

FIG. 5 is a second perspective view depicting the initial steps of the exemplary embodiment of FIG. 3.

FIG. 6 is a third perspective view depicting the intermediate steps of the exemplary embodiment of FIG. 3, and in particular, FIG. 6 illustrates the advancement of the inner catheter through the wall of the LAA and into the pericardial cavity surrounding the heart.

FIG. 7 is a fourth perspective view depicting the intermediate steps of the exemplary embodiment of FIG. 3, and in particular, FIG. 7 illustrates the further advancement of the inner catheter through the pericardial cavity and into a region adjacent to the xiphisternum.

FIG. 8A is a fifth perspective view depicting the intermediate steps of the exemplary embodiment of FIG. 3, and in particular, FIG. 8A illustrates the inner catheter being "pulled out" and exteriorized by way of electromagnetic forces.

FIG. 8B illustrates alternative sites for exteriorizing the inner catheter after it has been drawn from the pericardial site.

FIG. 9 is a sixth perspective view depicting the intermediate steps of the exemplary embodiment of FIG. 3, and in particular, FIG. 9 shows the deployment of the closure device being advanced over the exteriorized inner catheter and to the LAA ostium.

Figure 10:
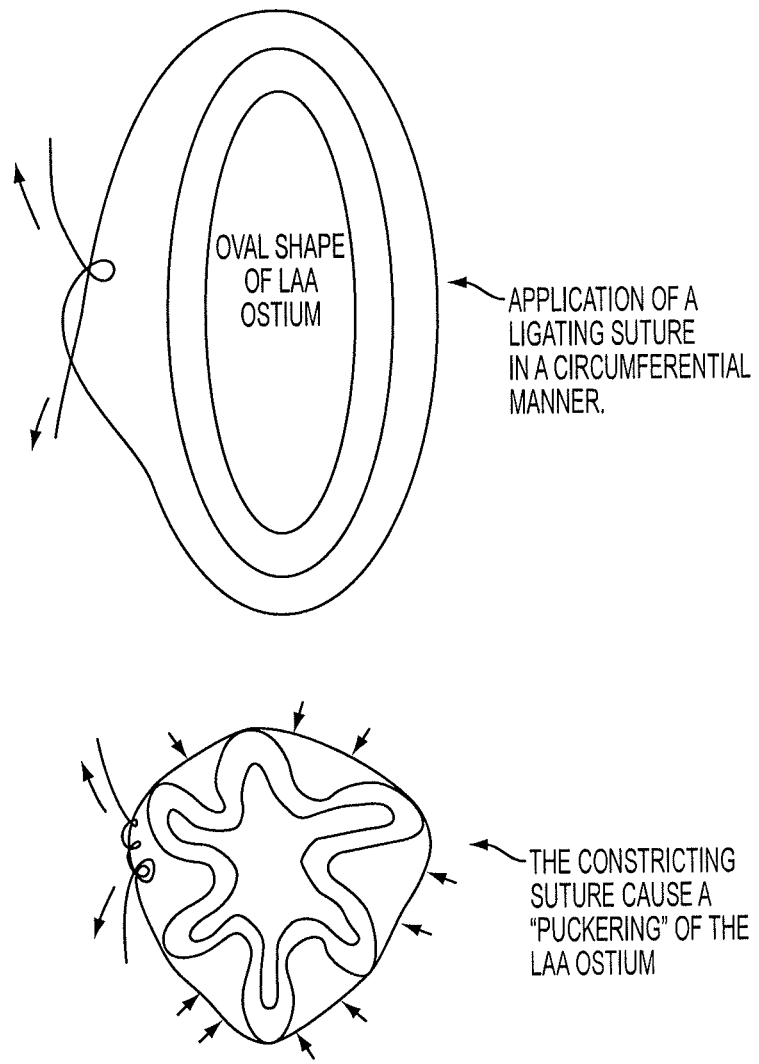
FIG. 10 illustrates a prior art closure device employing a loop or suture which results in puckering of the LAA ostium.

FIG. 10 illustrates a prior art closure device employing a loop or suture which results in puckering of the LAA ostium. With a ligating circumferentially applied suture, such as in a "purse string" manner, the fixed circumference of the LAA is now compressed by the suture into a smaller area. Hence, a puckering of the LAA ostium results. With puckering, communications are likely to occur between the left atrium and the LAA. The ostium of the LAA is likely to be incompletely occluded. This is especially true of the ostium of the LAA which is more an oval rather than a circular structure. The circumference or perimeter that remains fixed is being compressed into a smaller area by the constricting suture or tie. Furthermore, a circumferentially tied-suture is also more likely to cause a tear in the LAA wall. Therefore, puckering compromises the occlusion of the LAA and potentially allows the release of clot back into the left atrium.

FIG. 11 is a seventh perspective view depicting the intermediate steps of the exemplary embodiment of FIG. 3, and in particular, FIG. 9 illustrates the deployment of the closure device being deployed over the exterior of the LAA ostium without creating a puckering of the LAA ostium. With the application of a flat clip or similar closure, the circumference of the base of the LAA is not compressed into a smaller area and puckering does not result. Closure device 1300 is an example of a clip-like device. During deployment of closure device 1300, forces are applied along the short axis/diameter of the oval LAA ostium. Closure device 1300 applies forces along the short axis or short diameter of the oval or elliptical LAA ostium. Hence, a barrette or clip-like device such as closure device 1300 applied at the ostium of the LAA is more likely to seal off the structure. Force applied along the long diameter is less likely to approximate the opposite surfaces since (a) the two surfaces will have to travel a longer distance and (b) a greater amount of force will be necessary to overcome the elasticity/recoil of the tissue. Such a clip, such as closure device 1300, is also less likely to tear or lacerate the LAA than a suture.

FIG. 12 is an eighth perspective view depicting the intermediate steps of the exemplary embodiment of FIG. 3, and in particular, FIG. 12 illustrates the injury of the inner surface of the LAA prior to closure, where the injury causes an injury response which results in a more complete sealing along the opposed tissue surfaces.

As shown in FIG. 12, the inner wall of the LAA ostium will preferably be injured to induce to induce a tissue response that enhances closure and sealing. For example, thermal injury may be induced by circulating a hot fluid through inflated balloons 102 and 104 that are occluding the LAA. Alternatively, the LAA tissue may be injured or fused by applying RF current through inflated balloons 102 and 104, and/or the external closure device. Apposition of injured surfaces will cause "tissue welding," such as cross linking of the tissue collagen, resulting in a more complete closure. Other energy sources, such as high energy focused ultrasound, mechanical abrasion, laser or cryoablation, may also be used. The combination of pressure exerted by a clip or barrette and adhesions formed at the endocardial surface will exert a synergistic effect in ensuring that the occlusion at the LAA ostium is complete and persistent.

FIG. 13 illustrates the present invention's closure device, which is part of present invention's system for accessing a pericardial space and preventing strokes arising from the LAA. Closure device 1300 comprises suture 1301, and hollow tubes 1302 and 1303. Hollow tubes 1302 and 1303 are preferably semi-rigid tubes that are designed to function as a clip or a barrette when closed over the base of the LAA. The use of the flat clip or barrette structure is a significant advantage over using a suture loop or equivalent closure. As shown in FIG. 10, a circumferential suture applied in a "purse string" manner), compresses the base of the LAA into a smaller area causing puckering of the ostium. Such puckering compromises the occlusion and potentially allows the release of a clot back into the left atrium. With the application of a flat clip or similar closure, the circumference of the LAA ostium is not compressed into a smaller area and puckering does not result. During application of the clip-like device, forces are applied along the short axis/diameter of the oval LAA ostium.

An exemplary clip that approximates opposed surfaces of the LAA ostium is illustrated in FIG. 11. The clip applies forces along the short axis or short diameter of the oval or elliptical LAA ostium. Hence, a barrette or clip applied at the ostium of the LAA is more likely to seal off the structure. Force applied along the long diameter is less likely to approximate the opposite surfaces since (a) the two surfaces will have to travel a longer distance and (b) a greater amount of force will be necessary to overcome the elasticity/recoil of the tissue. Such a clip is also less likely to tear or lacerate the LAA than a suture.

Optionally, hollow tubes 1302 and 1303 may be coated over at least an inner surface with a hydrogel, silicone gel, and/or other biocompatible material. Hydrogels will expand on contact with water or blood to further compress the ostium of the LAA. It is possible that the thickness of the coating may vary and may be greater over the mid-portion of the tubes. The ability of the clip-like closures of the present invention to slide and adjust position over the LAA contributes to the stability and tight closure which is achieved.

FIG. 14 is a ninth perspective view depicting the intermediate steps of the exemplary embodiment of FIG. 3. FIG. 14 illustrates an anchoring mechanism to provide tension or traction to (a) facilitate the placement of closure device 1300 over the exterior of the LAA ostium, and (b) facilitate the deflation and removal of inflated balloons 102, 104, and 115, inner sheath 101 and outer sheath 103.

Figure 15:
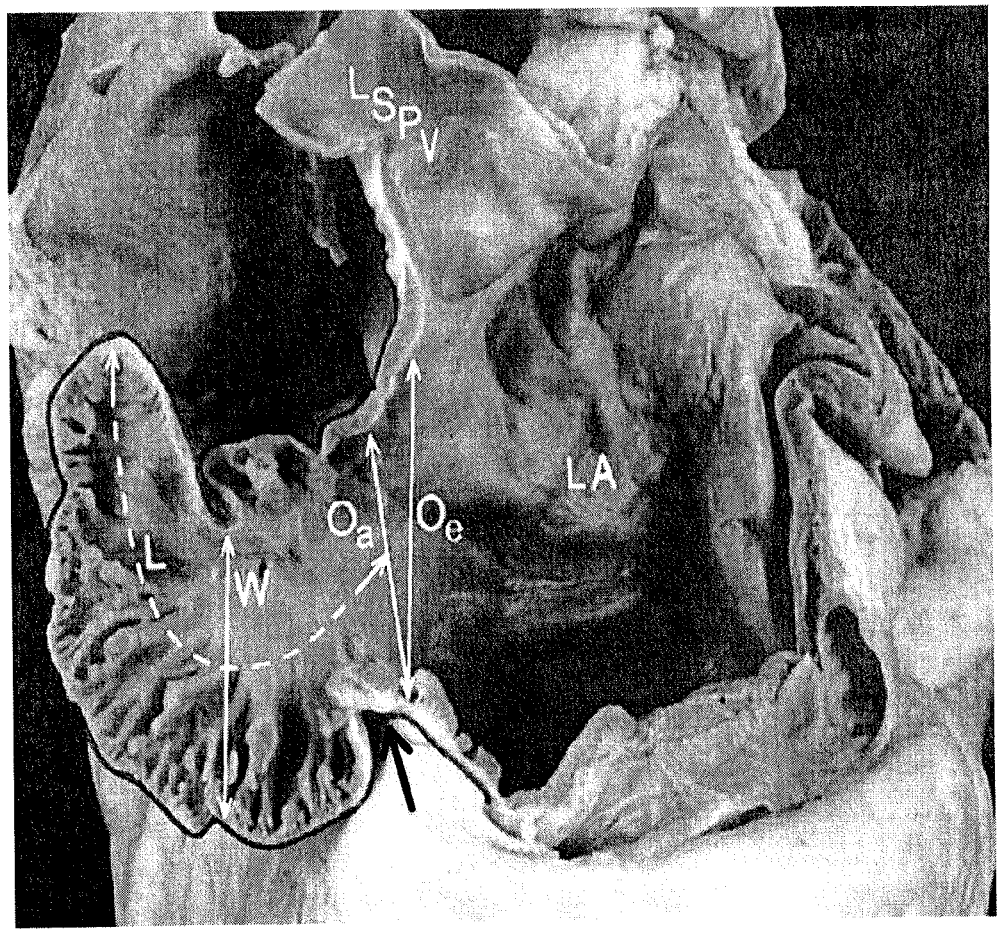
FIG. 15 is a photo depicting an exemplary anatomy of an LAA.

FIG. 15 is a photo depicting an exemplary anatomy of an LAA. LA is the left atrium. LSPV is the left superior pulmonary valve. L is the length of the LAA. W is the width of the LAA. $O_a$ is the diameter of the LAA ostium with respect to the rough-walled portions of the LAA. For example, upon inflation, balloon 102 is approximated against $O_a$. $O_e$ is the diameter of the LAA ostium with respect to the smooth-walled portions of the left atrial cavity. For example, upon inflation, balloon 103 is approximated against $O_e$. The upright arrow at the bottom shows an in-folding or constriction at the LAA ostium. However, this constriction is absent or less prominent at the opposite surface. In many specimens, a distinct circumferential constriction is absent at the ostium of the LAA. This raises the possibility that upon inflation of a balloon within the LAA, it may fall out of the LAA into the left atrial cavity. Inflated balloon 103 prevents inflated balloon 102 from falling into the left atrial cavity. Hence, the present invention provides for a plurality of inflatable balloons to create a more effective hemostatic seal.

Additionally, as shown in FIG. 15, nearly all LAA of an average adult contains pectinate muscles of greater than 1-mm in diameter. This gives the LAA a rough quality unlike the left atrial cavity, which is smooth-walled. Additionally, as shown in FIG. 15, deep recesses are presents within the LAA in-between the pectinate muscles. The presence of these recesses in-between the pectinate muscles make it difficult for a singular inflated balloon to effectively seal the LAA. Hence, the present invention provides for a plurality of inflatable balloons to create a more effective hemostatic seal.

FIG. 16 is an exemplary depiction of an LAA showing the presence of distinct protrusions termed lobes within the LAA. 1601 is the circumference of the LAA ostium. 1602, 1603, and 1604 are protrusions termed lobes and are located within the LAA. The presence of lobes 1602, 1603, and 1604 and the recesses in-between the pectinate muscles make it difficult for a singular inflated balloon to effectively seal the LAA. Hence, the present invention provides for a plurality of inflatable balloons to create a more effective hemostatic seal.

Figure 17:
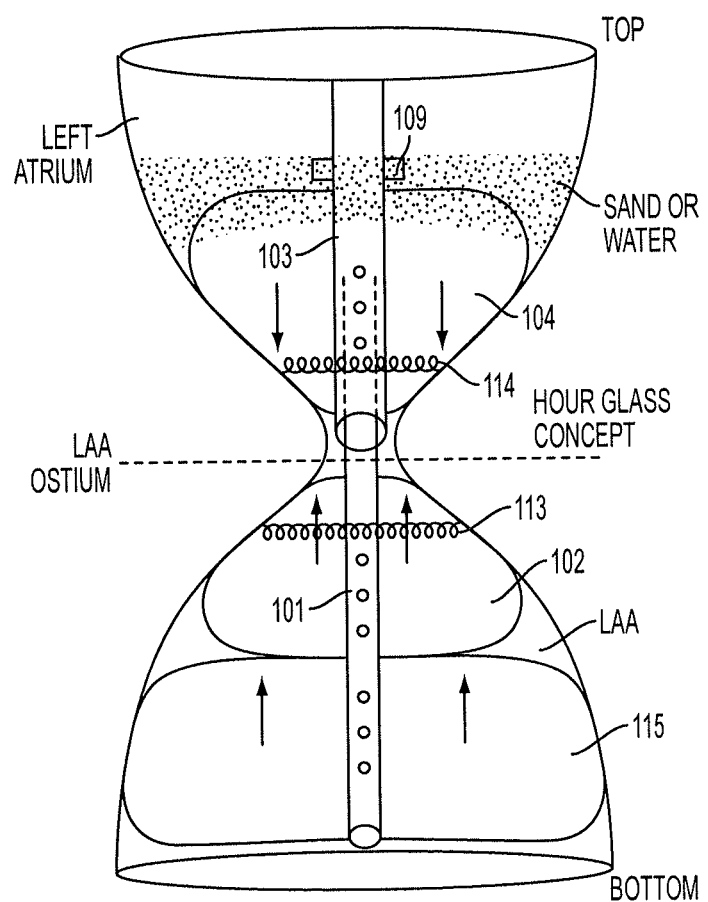
FIG. 17 is an exemplary depiction of an LAA in accordance with the hour-glass concept.

FIG. 17 is an exemplary depiction of an LAA in accordance with the hour-glass concept. One of the key factors affecting the time measured in the hour-glass is the neck width. The present invention is based on the concept that preventing the sand or water flowing from the top bulb to the bottom is achieved by occluding or sandwiching the neck by a combination of balloons rather by inflating one balloon in the bottom bulb only. The balloons (inflatable balloons 102 and 104) that are placed immediately across the neck are approximated towards each other by a combination of pushing and pulling. For example, inflatable balloon 102 is pushed upwards by inflatable balloon 115 and is pulled by manual traction on inner sheath 101 as well as by electromagnetic coils 114 applied from inflatable balloon 104. Inflatable balloon 104 is pushed towards the neck and towards inflatable balloon 102 by manual forces applied on outer sheath 103 and are also pulled by electromagnetic forces 113 applied from inflatable balloon 102. The top bulb represents the left atrial cavity while the bottom bulb represents the LAA. The neck represents the LAA ostium.

FIG. 18 is another exemplary depiction of an LAA in accordance with the hour-glass concept. The detailed description of FIG. 17 is equally applicable to FIG. 18. The top bulb represents the smooth-walled left atrial cavity while the bottom bulb of the hour glass represents the rough-walled LAA with the pectinate muscles and lobes. Upon inflation, inflatable balloons 102 and 115 are less likely to provide an effective hemostatic seal without inflatable balloon 104. Inflatable balloon 104 is approximated against the smooth-walled left atrial cavity. Inflatable balloon 104 serves as the key expanding element because (a) it prevents inflatable balloon 102 from falling into the left atrium, and (b) firmly occludes the LAA ostium to enhance the hemostatic seal. By way of electromagnetic coils 113, inflatable balloon 104 is pulled towards the neck of the hour-glass, which is the LAA ostium. Inflatable balloon 115 pushes inflatable balloon 102 towards the LAA ostium.

FIG. 19 is a tenth perspective view depicting the intermediate steps of the exemplary embodiment of FIG. 3, and in particular, FIG. 19 illustrates the accentuation of the waist of the LAA ostium and the wall of the proximal portion of the LAA caused by the inflation of the non-compliant balloon. For brevity, the detailed descriptions of steps 302 to 308 of FIG. 3 are incorporated by reference herein. Inflatable balloon 102 is inflated within the LAA interior adjacent to the LAA ostium. Inflatable balloon 102 is non-compliant and is inflated with higher pressure. As a non-compliant balloon, inflatable balloon 102 deforms and expands the walls of the LAA and in particular, the waist of the LAA. As shown in FIG. 19, the dotted line shows the expansion of these LAA walls and LAA waist by inflated balloon 102. The dotted line shows the expansion of these LAA walls and LAA waist. The LAA is more distensible than the left atrium and hence, should readily deform in response to a high pressure inflation of non-compliant balloon 102. After inflation, non-compliant balloon 102 is pulled towards the LAA ostium. Inflatable balloon 115 is inflated within the distal portion of the LAA interior and is largely compliant. Upon inflation, balloon 115 conforms to its surroundings in the LAA and pushes inflated balloon 102 towards the LAA ostium, as shown in FIG. 19. Additionally, inflated balloon 115 prevents inflated balloon 102 from being pushed away from the LAA ostium. Inflatable balloon 104 is inflated within the left atrium portion adjacent to the LAA ostium, as shown in FIG. 19. After inflation, balloon 104 is pushed towards the LAA ostium, and will prevent inflated balloon 102 from falling into the left atrium. Finally, inflated balloons 102 and 104 are manually pushed towards each other by pulling on the inner sheath and pushing on the outer sheath, respectively.

Alternatively, it is contemplated that one inflatable balloon can have multiple internal compartments within the balloon such that each internal compartment effectively operates as a separate inflatable balloon. For example, it is contemplated that one inflatable balloon can have three internal compartments such that each of these three internal compartments effectively operate in a similar manner as inflatable balloons 102, 104, and 115 shown in FIG. 19, respectively. Thus, upon inflation, this one inflatable balloon covers the area from (a) the region of the left atrium adjacent to the LAA ostium, to (b) the distal portions of the LAA interior, as currently achieved by the combination of inflatable balloons 102, 104, and 115 shown in FIG. 19.

FIG. 20 is a perspective view depicting an optional step of the exemplary embodiment of FIG. 3. Optionally, another embodiment of this method may include an additionally step between steps 309 and 310 of inflating an additional inflatable balloon 123 located on outer sheath 103, as shown in FIG. 20. Inflatable balloon 123 is attached to the distal end of outer sheath 103, and is inflated within a portion of the left atrium adjacent to the interatrial septum, as shown in FIG. 20. Alternatively, inflatable balloon 123 can be inflated adjacent to the *fossa ovalis*. This balloon serves as an anchor to render stationary inflated balloon 104 and prevent outer sheath 103 from getting pulled back.

What is claimed:

1. A method for accessing a pericardial cavity and preventing strokes arising from a left atrial appendage (LAA), said method comprising:
   introducing a catheter into a body cavity, wherein the catheter comprises an inner sheath, an outer sheath, and an inner catheter;
   advancing a distal end of the inner sheath to position the distal end of the inner sheath in an interior of the LAA;
   inflating a first inflatable balloon, wherein the first inflatable balloon is on the distal end of the inner sheath, wherein the first inflatable balloon is non-compliant, and wherein the first balloon is inflated within the LAA interior adjacent to an ostium of the LAA;
   pulling the inflated first balloon in a direction from within the LAA interior and towards the LAA ostium;
   inflating a second inflatable balloon, wherein the second balloon is on the distal end of the inner sheath, wherein the second balloon is inflated within a distal portion of the LAA interior, and wherein upon inflation, the inflated second balloon pushes the inflated first balloon towards the LAA ostium;

advancing a distal end of the outer sheath to position the distal end of the outer sheath in a portion of the left atrium adjacent to the LAA ostium;

inflating a third inflatable balloon, wherein the third balloon is on the distal end of the outer sheath, and wherein the third balloon is inflated within a portion of the left atrium adjacent to the LAA ostium;

pushing the inflated third balloon in a direction from within the left atrium portion adjacent to the LAA ostium and towards the LAA ostium;

activating a locking mechanism to lock the outer sheath with the inner sheath, thereby rendering stationary the inflated balloons;

advancing a distal end of the inner catheter to position the distal end of the inner catheter within a distal portion of the LAA interior near an apex of the LAA;

puncturing a wall of the LAA interior near or at the LAA apex using a tissue-penetrating tip, wherein the tissue-penetrating tip is on the distal end of the inner catheter;

advancing the distal end of the inner catheter into and through the pericardial cavity to position the distal end of the inner catheter at a desired site of exteriorization;

puncturing a wall of the pericardial cavity at the desired site of exteriorization using the tissue-penetrating tip;

externalizing the inner catheter at the desired site of exteriorization;

advancing a proximal end of the inner catheter to the distal portion of the LAA near the LAA apex;

inflating a fourth inflatable balloon, wherein the fourth balloon is on the proximal end of the inner catheter, and wherein the fourth balloon is inflated within the distal portion of the LAA interior near the LAA apex;

pulling the inflated fourth balloon in a direction from within the distal portion of the LAA interior near the LAA apex and towards the pericardial cavity to anchor the LAA;

advancing a closure device towards the LAA ostium via the externalized inner catheter to position the closure device over the exterior of the LAA ostium; and deploying the closure device over the exterior of the LAA ostium.

2. The method of claim 1, further comprising the step of:
injuring at least a portion of an interior surface of the LAA ostium.

3. The method of claim 2, wherein at the step of injuring at least the portion of the interior surface of the LAA ostium, the injuring is achieved by delivering a heated liquid through the first and third inflated balloons.

4. The method of claim 2, wherein at the step of injuring at least the portion of the interior surface of the LAA ostium, the injuring is achieved by delivering radiofrequency current through the first and third inflated balloons.

5. The method of claim 1, further comprising the steps of:
deflating the first inflated balloon;
deflating the second inflated balloon;
deflating the third inflated balloon;
deactivating the locking mechanism;
removing the outer sheath from the body cavity; and
removing the inner sheath from the body cavity.

6. The method of claim 1, wherein at the steps of inflating the first and the third inflatable balloons, the first inflatable balloon has a first set of electromagnetic coils located within the first balloon, the third inflatable balloon has a second set of electromagnetic coils located within the third balloon, and upon inflation of the first and third balloons, the respective set of electromagnetic coils also expands with the respective balloon.

7. The method of claim 1, wherein at the step of advancing the distal end of the inner catheter to the desired site of exteriorization, the desired site of exteriorization is near a base of a sternum so that the inner catheter follows a subxiphoid path.

8. The method of claim 1, wherein at the step of advancing the distal end of the inner catheter to the desired site of exteriorization, the desired site of exteriorization is a pectoral region.

9. The method of claim 1, wherein at the step of externalizing the inner catheter at the desired site of exteriorization, the inner catheter is externalized by applying a magnetic force to pull the distal end of the inner catheter through the pericardial cavity and outwardly through a punctured skin.

10. The method of claim 1, wherein at the step of deploying the closure device over the exterior of the LAA ostium, the closure device is a suture looped through a pair of semi-rigid hollow tubes, wherein upon the deployment of the closure device, the pair of semi-rigid hollow tubes are clamped along a short diameter of the exterior of the LAA ostium, and the suture is tightened.

11. The method of claim 1, further comprising the step of inflating a fifth inflatable balloon, wherein the fifth balloon is on the distal end of the outer sheath, and wherein the fifth balloon is inflated within a portion of the left atrium adjacent to an interatrial septum.

* * * * *